(12) United States Patent
Okamura

(10) Patent No.: US 7,760,856 B2
(45) Date of Patent: *Jul. 20, 2010

(54) RADIOGRAPHIC APPARATUS AND RADIATION DETECTION SIGNAL PROCESSING METHOD

(75) Inventor: Shoichi Okamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 49 days.

This patent is subject to a terminal disclaimer.

(21) Appl. No.: 12/280,150

(22) PCT Filed: Feb. 20, 2006

(86) PCT No.: PCT/JP2006/302958

§ 371 (c)(1),
(2), (4) Date: Aug. 20, 2008

(87) PCT Pub. No.: WO2007/096937

PCT Pub. Date: Aug. 30, 2007

(65) Prior Publication Data

US 2009/0034679 A1    Feb. 5, 2009

(51) Int. Cl.
H05G 1/64 (2006.01)
(52) U.S. Cl. .............. 378/98.7; 378/19; 378/98.11; 378/98.8; 378/901
(58) Field of Classification Search .............. 378/4–20, 378/62, 98.11, 98.12, 987, 98.8, 207, 901; 250/370.08, 370.09, 370.11
See application file for complete search history.

(56) References Cited

U.S. PATENT DOCUMENTS

| | | | |
|---|---|---|---|
| 5,249,123 A | 9/1993 | Hsieh | |
| 5,563,421 A | 10/1996 | Lee et al. | |
| 7,073,941 B2 * | 7/2006 | Okamura | 378/207 |
| 7,313,218 B2 * | 12/2007 | Okamura et al. | 378/22 |
| 7,377,691 B2 * | 5/2008 | Okamura et al. | 378/207 |
| 7,460,643 B2 * | 12/2008 | Okamura | 378/98.8 |
| 2004/0156481 A1 | 8/2004 | Okamura et al. | |
| 2005/0031079 A1 * | 2/2005 | Okamura et al. | 378/91 |
| 2005/0031088 A1 * | 2/2005 | Okamura et al. | 378/210 |
| 2009/0010392 A1 * | 1/2009 | Okamura | 378/98.12 |

FOREIGN PATENT DOCUMENTS

| | | |
|---|---|---|
| JP | 09-009153 A | 1/1997 |
| JP | 2004-242741 A | 9/2004 |
| JP | 2005-283422 A | 10/2005 |
| JP | 2006-006387 A | 1/2006 |

OTHER PUBLICATIONS

International Search Report for the Application No. PCT/JP2006/302958 mailed Mar. 20, 2006.

* cited by examiner

*Primary Examiner*—Courtney Thomas
(74) *Attorney, Agent, or Firm*—Cheng Law Group, PLLC

(57) ABSTRACT

A radiographic apparatus according to this invention, when a predetermined operation relating to radiographic imaging is interposed during an emission of radiation, stops the emission temporarily, and also stops a recursive computation temporarily. With start of the predetermined operation, the emission is started again and also the recursive computation is started again. Radiation detection signals at the time of non-emission due to the temporary stop are acquired, and the recursive computation is carried out based on initial values derived from the radiation detection signals at the time of non-emission. The lag-behind parts are removed from the radiation detection signals with increased accuracy while reducing the trouble of radiographic images caused by the predetermined operation relating to radiographic imaging being interposed during an emission of radiation.

14 Claims, 9 Drawing Sheets

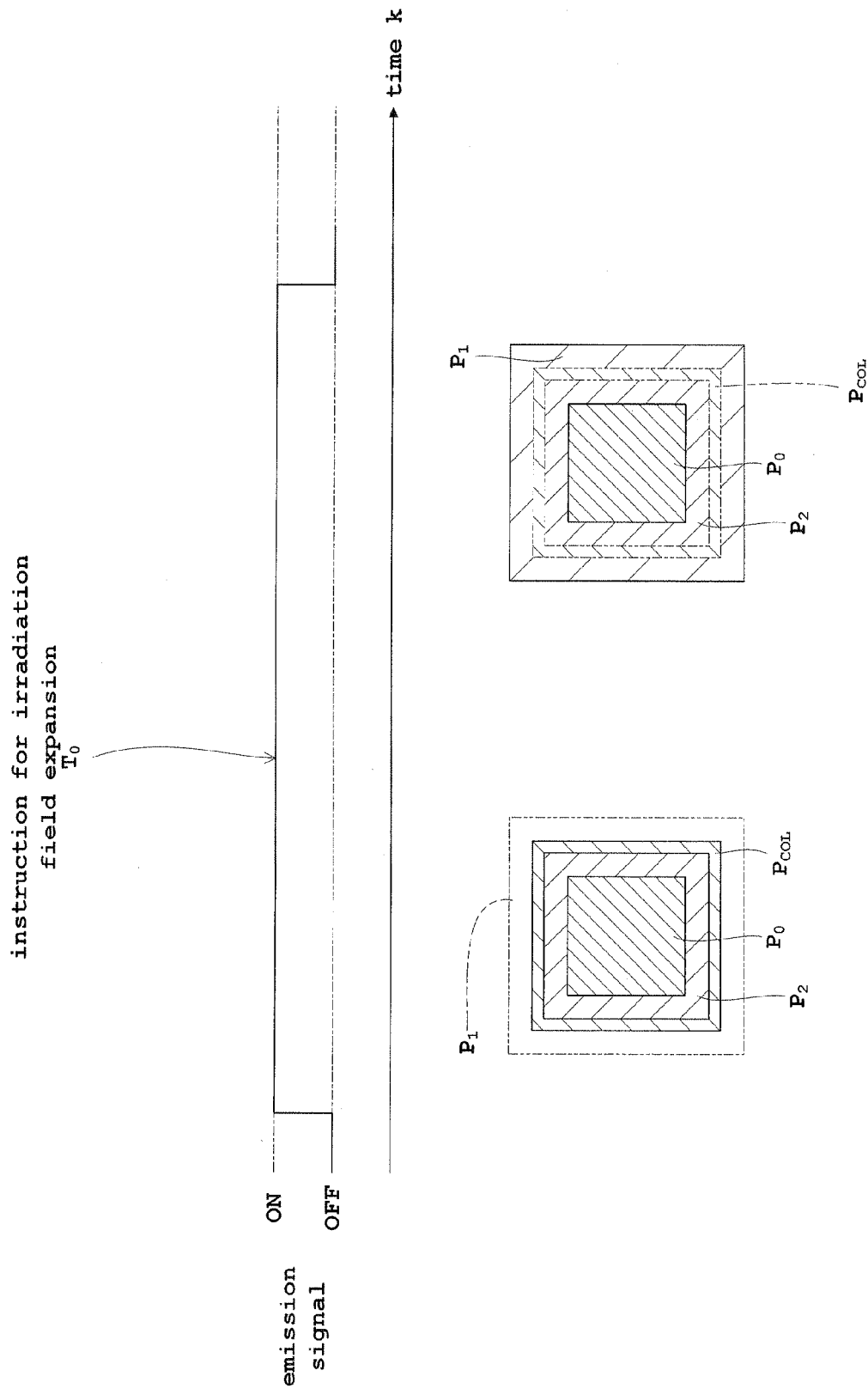

RADIOGRAPHIC APPARATUS AND RADIATION DETECTION SIGNAL PROCESSING METHOD

TECHNICAL FIELD

This invention relates to a radiographic apparatus for medical or industrial use and a radiation detection signal processing method, for obtaining radiographic images based on radiation detection signals outputted at predetermined sampling time intervals from a radiation detecting device as radiation is emitted to an object under examination. More particularly, the invention relates to a technique for eliminating time lags, due to the radiation detecting device, of the radiation detection signals taken from the radiation detecting device.

BACKGROUND ART

In a medical X-ray diagnostic apparatus which is a typical example of radiographic apparatus, a flat panel X-ray detector (hereinafter called "FPD" as appropriate) has recently been used as an X-ray detecting device for detecting X-ray penetration images of a patient resulting from X-ray emission from an X-ray tube. The FPD includes numerous semiconductor or other X-ray detecting elements arranged longitudinally and transversely on an X-ray detecting surface.

That is, the X-ray diagnostic apparatus is constructed to obtain, based on X-ray detection signals for one X-ray image taken at sampling time intervals from the FPD as a patient is irradiated with X rays from the X-ray tube, an X-ray image corresponding to an X-ray penetration image of the patient for every period between sampling intervals. The use of the FPD is advantageous in terms of apparatus construction and image processing since the FPD is lighter and less prone to complicated detecting distortions than the image intensifier used heretofore.

However, the FPD has a drawback of causing time lags whose adverse influence appears in X-ray images. Specifically, when X-ray detection signals are taken from the FPD at short sampling time intervals, the remainder of a signal not picked up adds to a next X-ray detection signal as a lag-behind part. Thus, where X-ray detection signals for one image are taken from the FPD at 30 sampling intervals per second to create X-ray images for dynamic display, the lag-behind part appears as an after-image on a preceding screen to produce a double image. This results in an inconvenience such as blurring of dynamic images.

U.S. Pat. No. 5,249,123 discloses a proposal to solve the problem of the time lag caused by the FPD in acquiring computer tomographic images (CT images). This proposed technique employs a computation for eliminating a lag-behind part from each of radiation detection signals taken from an FPD at sampling time intervals $\Delta t$.

That is, in the above U.S. patent, a lag-behind part included in each of the radiation detection signals taken at the sampling time intervals is assumed due to an impulse response formed of a plurality of exponential functions, and the following equation is used to derive radiation detection signal $x_k$ with a lag-behind part removed from radiation detection signal $y_k$:

$$x_k = [y_k - \Sigma_{n=1}^{N}[\alpha_n \cdot [1-\exp(T_n)] \cdot \exp(T_n) \cdot S_{nk}]]/\Sigma_{n=1}^{N}\beta_n$$

in which $T_n = -\Delta t/\tau_n$, $S_{nk} = x_{k-1} + \exp(T_n) \cdot S_{n(k-1)}$, and $\beta_n = \alpha_n \cdot [1-\exp(T_n)]$, where $\Delta t$: sampling intervals;

k: subscript representing a k-th point of time in a sampling time series;

N: the number of exponential functions with different time constants forming the impulse response;

n: subscript representing one of the exponential functions forming the impulse response;

$\alpha_n$: intensity of exponential function n; and $\tau_n$: attenuation time constant of exponential function n.

Inventors herein have tried the computation technique proposed in the above U.S. patent. However, the only result obtained is that the above technique cannot avoid artifacts due to the time lag and satisfactory X-ray images cannot be obtained. It has been confirmed that the time lag due to the FPD is not eliminated (Patent Document 1).

Then, Inventors have previously proposed a technique in Unexamined Patent Publication No. 2004-242741. In dealing with the time lag of the FPD, this technique removes a lag-behind part due to an impulse response based on the following recursive equations a-c:

$$X_k = Y_k - \Sigma_{n=1}^{N}[\alpha_n \cdot [1-\exp(T_n)] \cdot \exp(T_n) \cdot S_{nk}] \qquad a$$

$$T_n = -\Delta t/\tau_n \qquad b$$

$$S_{nk} = X_{k-1} + \exp(T_n) \cdot S_{n(k-1)} \qquad c$$

where $\Delta t$: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n;

$S_{n0} = 0$; and $X_0 = 0$.

In this recursive computation, coefficients of the impulse response of the FPD, N, $\alpha_n$ and $\tau_n$, are determined in advance. With the coefficients fixed, X-ray detection signal $Y_k$ is applied to equations a-c, thereby obtaining a lag-free X-ray detection signal $X_k$ (Patent Document 2). The above correction for removing the lag-behind part is also called "lag correction".

Besides the above technique of Patent Document 2, there is a technique of using backlight to reduce long time constant components of lag-behind parts (see Patent Document 3, for example).

Incidentally, a 17-inch size FPD, for example, has 3072×3072 pixels arranged vertically and horizontally, and the above technique of Patent Document 2 requires an enormous calculation amount for recursive computation. Thus, in fluoroscopy of dynamic images, a binning operation is carried out to add pixels as a measure for reducing calculation amounts. In a binning operation to combine 2×2 vertical and horizontal pixels into one, for example, the number of pixels is decreased to one fourth by the binning operation, thereby reducing the calculation amount to one fourth. In a binning operation to combine 4×2 pixels, i.e. 4 vertical pixels and 2 horizontal pixels, into one, the number of pixels is decreased to one eighth by the binning operation, thereby reducing the calculation amount to one eighth.

When a small number of pixels are binned, an image acquired has high resolution, and when a large number of pixels are binned, an image acquired has low resolution. Therefore, when greater importance is given to reducing a calculation amount than to obtaining an image of high resolution, an increased number of pixels are binned to acquire an image of low resolution, thereby reducing the calculation amount. Conversely, when greater importance is given to obtaining an image of high resolution than to reducing a calculation amount, the calculation amount is increased to bin a small number of pixels and acquire an image of high resolution.

On the other hand, a calculation amount is increased or decreased by changing the size of an irradiation field of X rays with a collimator to change an image range forming a subject of recursive computation. When an expansion is made from an irradiation field 12 inches square to an irradiation field 15 inches or 17 inches square, for example, the calculation amount increases from the case of 12 inches square by an amount corresponding to the expansion of the image range forming the subject of recursive computation. Conversely, when a reduction is made from the irradiation field 12 inches square to an irradiation field 9 inches square, the calculation amount decreases from the case of 12 inches square by an amount corresponding to the reduction of the image range forming the subject of recursive computation.

Thus, the frame rate of dynamic images is maintained by preparing beforehand a plurality of modes having combinations of irradiation field and binning, and switching the modes as required by the operator. Therefore, when an observation is made by means of images of high resolution, the irradiation field is reduced in size in order to suppress increase in the calculation amount due to a decreased number of pixels subjected to binning. When an observation is made by means of images of high resolution, for example, a 2×1 binning is used, and on the other hand a mode is used for restricting the irradiation field to 9 inches square. Conversely, an observation is made by means of images of large irradiation field, a decreased number of pixels are subjected to binning in order to suppress increase in the calculation amount due to an enlarged irradiation field. When an observation is made by means of images of large irradiation field, for example, the irradiation field is enlarged to 17 inches square, and on the other hand a mode is used for restriction to a low resolution of 4×2 binning.

[Patent Document 1]
U.S. Pat. No. 5,249,123 (mathematical expressions in the specification and the drawings)

[Patent Document 2]
Unexamined Patent Publication No. 2004-242741 (mathematical expressions in the specification and the drawings)

[Patent Document 3]
Unexamined Patent Publication H9-9153 (pages 3-8, FIG. 1)

DISCLOSURE OF THE INVENTION

Problem to be Solved by the Invention

However, there is a problem that, at a time of the above irradiation field expansion, high brightness due to time constant components of lag-behind parts (called "lag components") remains in an outer frame portion of an irradiation field before the irradiation field expansion. This problem will be described with reference to FIGS. 11 and 12. FIG. 11 is a view schematically showing images before and after an irradiation field expansion. FIG. 12 is a view showing, in a time series relationship, irradiation situations and images before and after the irradiation field expansion.

As shown in FIG. 11, $P_0$ denotes an image before the irradiation field expansion, $P_1$ denotes an image after the irradiation field expansion, $P_{COL}$ denotes an image portion corresponding to a collimator, and $P_2$ denotes an outer frame portion between the image $P_0$ before the irradiation field expansion and the image portion $P_{COL}$ corresponding to the collimator. As shown in FIG. 12, $T_0$ denotes timing of an instruction for irradiation field expansion. An emission signal at the time of ON in FIG. 12 represents an irradiating state of radiation, and an emission signal at the time of OFF represents a non-irradiation state of radiation. Description will be made by taking an image of irradiation field 12 inches square as an example of the image $P_0$ before the irradiation field expansion, and taking an image of irradiation field 15 inches square as an example of the image $P_1$ after the irradiation field expansion.

Before the irradiation field expansion, a lag correction is carried out to remove lag-behind parts by recursive computation after starting irradiation with radiation (see the shift from OFF to ON in FIG. 12), with the collimator restricted to a size (e.g. 13 inches) slightly larger than the irradiation field 12 inches square. At this time, the image range forming the subject of the recursive computation is the range of image $P_0$ before the irradiation field expansion which is the irradiation field 12 inches square. On the other hand, although the outer frame portion $P_2$ is outside the subject of the recursive computation, it is within the collimator restricted to the size slightly larger than the irradiation field 12 inches square. Thus, the outer frame portion $P_2$ is irradiated all the time with the irradiation not obstructed by the collimator.

Thus, the (12-inch) image $P_0$ before the irradiation field expansion which is the subject of recursive computation undergoes a lag correction by recursive computation, and therefore no lag components will remain thereon. The outer frame portion $P_2$ is left in the irradiated state with no recursive computation carried out therefor, and lag components are accumulated thereon. The outer frame portion $P_2$ does not pose a problem since only the (12-inch) image $P_0$ before the irradiation field expansion is observed before the irradiation field expansion. The moment an expansion to the irradiation field 15 inches square is made on an instruction for irradiation field expansion (see $T_0$ in FIG. 12), the lag components superimposed on the outer frame portion $P_2$ will appear as high brightness.

Therefore, at the time of irradiation field expansion, the lag components become superimposed on the outer frame portion $P_2$ of the irradiation field before the irradiation field expansion, and radiation detection signals will have high signal values (high pixel values) owing to the lag components. The high brightness remaining in the outer frame portion $P_2$ will cause a problem with a radiographic image. Thus, the radiographic image has a problem when a predetermined operation relating to radiographic imaging, typically the irradiation field expansion, is interposed during radiation emission.

Incidentally, since this high brightness is the more outstanding with an FPD having the larger long time constant components (called the "long-term lags") of lag-behind parts, measures are taken to tighten the acceptability criteria for lag characteristics at the time of delivery inspection so that FPDs with high brightness may not be shipped. However, tightening of the acceptability criteria brings about a drawback in yield improvement of FPDs.

It is possible to ship products with nothing done about such unnatural high brightness. In that case, a certain amount of waiting time will be needed until attenuation of the high brightness. This will result in an extended time of exposure to radiation of patients, an extended examination time, or an obstruction to diagnosis by doctors. Thus, there is a need for a method of removing the unnatural high brightness without increasing an arithmetic load even for FPDs with lag characteristics comparable to those existing heretofore.

This invention has been made having regard to the state of the art noted above, and its object is to provide a radiographic apparatus and a radiation detection signal processing method capable of eliminating time lags, due to a radiation detecting device, from radiation detection signals taken from the radiation detecting device, while reducing drawbacks in a radiographic image caused by a predetermined operation relating to radiographic imaging interposed during radiation emission.

Means for Solving the Problem

To fulfill the above object, this invention provides the following construction.

A radiographic apparatus of this invention is a radiographic apparatus for obtaining radiographic images based on radiation detection signals, comprising a radiation emitting device for emitting radiation toward an object under examination, a radiation detecting device for detecting radiation transmitted through the object under examination, and a signal sampling device for taking radiation detection signals from the radiation detecting device at predetermined sampling time intervals, said apparatus being constructed to obtain radiographic images based on the radiation detection signals outputted from the radiation detecting device at the predetermined sampling time intervals as radiation is emitted to the object under examination, said apparatus further comprising a time lag removing device for removing lag-behind parts from the radiation detection signals by a recursive computation, on an assumption that a lag-behind part included in each of said radiation detection signals taken at the predetermined sampling time intervals is due to an impulse response formed of a single or a plurality of exponential functions with different attenuation time constants; and an emission control device for controlling timing of emission start and emission stop of said radiation emitting device; characterized in that (A) in a state where the emission control device having caused the radiation emitting device to start emission, said time lag removing device removes the lag-behind parts by recursive computation to obtain corrected radiation detection signals, (B) in response to an instruction for a predetermined operation relating to radiographic imaging, the emission control device causes said radiation emitting device to stop the emission temporarily, the time lag removing device stops the recursive computation temporarily, and said signal sampling device acquires radiation detection signals in time of non-emission due to the temporary stop of the radiation emitting device, and (C) with start of said predetermined operation, the emission control device causes the radiation emitting device to start emission again, and the time lag removing device starts the recursive computation again based on initial values derived from the radiation detection signals in time of said non-emission.

In the radiographic apparatus according to this invention, the time lag removing device removes lag-behind parts included in the radiation detection signals outputted from the radiation detecting device at the predetermined sampling time intervals as radiation is emitted to the object under examination by the radiation emitting device, as being due to an impulse response formed of a single or a plurality of exponential functions with different attenuation time constants. A lag-behind part is removed from each radiation detection signal is removed through a recursive computation. The process of removal from each radiation detection signal is executed following the following steps That is, (A) with the radiation emitting device caused to start emission by the emission control device which controls the timing of emission start and emission stop of the radiation emitting device, the time lag removing device removes a lag-behind part by recursive computation to obtain a corrected radiation detection signal. And, (B) on an instruction for a predetermined operation relating to radiographic imaging, the emission control device causing the radiation emitting device to stop the emission temporarily, the time lag removing device stops the recursive computation temporarily, and the signal sampling device acquires radiation detection signals in time of non-irradiation with the temporary stop of the radiation emitting device. Further, (C) with start of the above predetermined operation, the emission control device causes the radiation emitting device to start emission again, and the time lag removing device starts the recursive computation again based on initial values derived from the radiation detection signal in time of non-emission. Before the predetermined operation, the time lag removing device removes lag-behind parts by recursive computation, thereby to acquire radiographic images from the corrected radiation detection signals obtained. After the predetermined operation, the time lag removing device removes lag-behind parts by the recursive computation based on the above initial values, thereby to acquire radiographic images from the corrected radiation detection signals obtained.

Thus, according to the radiographic apparatus of this invention, when the predetermined operation noted above is interposed during radiation emission, the emission is stopped temporarily, and also the recursive computation is stopped temporarily, as in (B) noted above. With start of the predetermined operation, emission is started again, and the recursive computation also is started again based on the initial values derived from the radiation detection signals in time of non-emission, as in (C) noted above. Therefore, in (C), emission and recursive computation can be carried out after the predetermined operation as before the predetermined operation. With the temporary stop in (B), the emission and recursive computation before the predetermined operation do not impart influence on the data after the predetermined operation. On the other hand, the sampling device acquires radiation detection signals at the time of non-emission due to the temporary stop as in (B), and a recursive computation is carried out based on the initial values derived from the radiation detection signals at the time of non-emission as in (C). Even if the predetermined operation noted above is interposed during radiation emission, lag-behind parts can be removed from the radiation detection signals with increased accuracy while reducing the trouble of radiographic images caused by the predetermined operation relating to radiographic imaging interposed during radiation emission.

A radiation detection signal processing method of this invention is a radiation detection signal processing method for taking, at predetermined sampling time intervals, radiation detection signals detected after irradiation of an object under examination, and carrying out signal processing to obtain radiographic images based on the radiation detection signals outputted at the sampling time intervals, characterized in that the radiation detection signal processing method carries out a process of removing lag-behind parts from the radiation detection signals by a recursive computation, on an assumption that a lag-behind part included in each of said radiation detection signals taken at the predetermined sampling time intervals is due to an impulse response formed of a single or a plurality of exponential functions with different attenuation time constants, according to the following steps: (A) in a state where an emission of radiation is started, the lag-behind parts are removed by said recursive computation to obtain corrected radiation detection signals, (B) in response to an instruction for a predetermined operation relating to radiographic imaging, the emission is stopped temporarily, and the recursive computation is stopped temporarily, to acquire radiation detection signals in time of non-emission due to the temporary stop, and (C) with start of said predetermined operation, emission is again, and the recursive computation is started again based on initial values derived from the radiation detection signals in time of said non-emission.

According to the radiation detection signal processing method of this invention, when a predetermined operation relating to radiographic imaging is interposed during radiation emission, the emission is stopped temporarily, and also the recursive computation is stopped temporarily, as in (B) noted above. With start of the predetermined operation, emission is started again, and the recursive computation also is started again based on the initial values derived from the radiation detection signals in time of non-emission, as in (C) noted above. Therefore, in (C), emission and recursive computation can be carried out after the predetermined operation as before the predetermined operation. With the temporary stop in (B), the emission and recursive computation before the predetermined operation do not impart influence on the data after the predetermined operation. On the other hand, radiation detection signals at the time of non-emission due to the temporary stop are acquired as in (B), and a recursive computation is carried out based on the initial values derived from the radiation detection signals at the time of non-emission as in (C). Even if the predetermined operation noted above is interposed during radiation emission, lag-behind parts can be removed from the radiation detection signals with increased accuracy while reducing the trouble of radiographic images caused by the predetermined operation relating to radiographic imaging during radiation emission.

One example of these radiographic apparatus and radiation detection signal processing noted above is as follows.

The recursive computation is carried out, before the predetermined operation noted above, for removing the lag-behind parts from the radiation detection signals, based on the following equations A-C:

$$X_k = Y_k - \Sigma_{n=1}^{N}[S_{nk}] \qquad A$$

$$T_n = -\Delta t/\tau_n \qquad B$$

$$S_{nk} = \exp(T_n) \cdot \{\alpha_n \cdot [1-\exp(T_n)] \cdot \exp(T_n) \cdot S_{n(k-1)}\} \qquad C$$

where $\Delta t$: the sampling time interval;

k: a subscript representing a k-th point of time in a sampling time series;

$Y_k$: a radiation detection signal taken at the k-th sampling time;

$X_k$: a corrected radiation detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n;

to determine the initial values for the recursive computation as in the following equation D:

$$X_0 = 0, S_{n0} = \gamma_n \cdot Y_0 \qquad D$$

where $\gamma_n$: residual rate of component n of certain attenuation time constant $\tau_n$, and $Y_0$: lag signal value remaining at the radiation non-emission time serving as the base point for the recursive computation before said predetermined operation; and to obtain the corrected radiation detection signals by removing the lag-behind parts based on said impulse response derived from said equations A-C with conditions of the initial values determined from said equation D.

According to this example, the corrected, lag-free radiation detection signal $X_k$ is derived promptly from equations A-C constituting a compact recurrence formula before the predetermined operation noted above.

Here, it is time k=0 that serves as the base point for the recursive computation, i.e. the radiation non-emission time for the first frame. $X_k$ and $S_{nk}$ at the time of k=0, i.e. initial values, when carrying out the recursive computation, are determined as in the above equation D. As shown in FIG. 10, for example, when a lag of the radiography in time t0-t1 is superimposed on fluoroscopy, a residual lag (lag signal value) due to a lag-behind part generated by the radiography in time t0-t1 exists even at the radiation non-emission time (see k=0 in FIG. 10) which is the basic point for the recursive computation. That is, the initial value $Y_0$ of radiation detection signal $Y_k$ is not 0 even at the radiation non-emission time.

Then, initial values for the recursive computation are set according to equation D, i.e. $X_0 = 0$, $S_{n0} = \gamma_n \cdot Y_0$ ($Y_0$: lag signal value remaining at the radiation non-emission time serving as the base point for the recursive computation). A corrected radiation detection signal $X_k$ is obtained by removing the lag-behind part based on the impulse response derived from equations A-C with conditions of the initial values determined from equation D.

One example of the predetermined operation noted above is an irradiation field expansion. In the case of irradiation field expansion, the above (B) is arranged to execute the above stop (of the emission and recursive computation) and acquire the radiation detection signals in time of the above non-emission (due to the temporary stop) in response to an instruction for the irradiation field expansion, and the above (C) is arranged to execute the restart (of the emission and recursive computation) with start of the irradiation field expansion, whereby, after the irradiation field expansion, the lag-behind parts are removed by the recursive computation based on the initial values derived from the radiation detection signals in time of the above non-emission, to obtain the corrected radiation detection signals.

In this case, an irradiation field expansion is interposed during radiation emission, the emission is stopped temporarily, and also the recursive computation is stopped temporarily, as in (B) noted above. With start of the irradiation field expansion, emission is started again, and the recursive computation also is started again, as in (C) noted above. Therefore, in (C), emission and recursive computation can be carried out after the irradiation field expansion as before the irradiation field expansion. With the temporary stop in (B), the emission and recursive computation before the irradiation field expansion do not impart influence on the data after the irradiation field expansion. On the other hand, radiation detection signals at the time of non-emission due to the temporary stop are acquired as in (B), and a recursive computation is carried out based on the initial values derived from the radiation detection signals at the time of non-emission as in (C). Even if the irradiation field expansion noted above is interposed during radiation emission, lag-behind parts can be removed from the radiation detection signals with increased accuracy while reducing the trouble of radiographic images caused by the irradiation field expansion interposed during radiation emission.

Particularly where the size of the irradiation field is controlled to be larger before said irradiation field expansion than an image subjected to the recursive computation, and smaller after the irradiation field expansion than the image subjected to the recursive computation, the following effect is realized. Before the irradiation field expansion, an image larger than an image to be subjected to the recursive computation and smaller than an image to be subjected to the recursive computation after the irradiation field expansion is an image excluding an image of the portion corresponding to an irradiation field control device from the image after the irradiation field expansion (i.e. the image to be subjected to the recursive computation after the irradiation field expansion), and also an image combining the image before the irradiation field expansion (i.e. the image to be subjected to the recursive computation before the irradiation field expansion) and the outer frame portion present between the image before the irradiation field expansion and the image of the portion corresponding to the irradiation field control device.

In the prior art, the outer frame portion not subjected to a recursive computation is left in the irradiated state before and after an irradiation field expansion. With the temporary stop in (B) noted above, the emission and recursive computation before the irradiation field expansion do not impart influence on the data of the outer frame portion after the irradiation field expansion. On the other hand, radiation detection signals at the time of non-emission due to the temporary stop are acquired as in (B), and a recursive computation is carried out based on initial values derived from the radiation detection signals at the time of non-emission as in (C). Thus, lag-behind parts due to the recursive computation can be removed with the above initial values with increased accuracy also for the outer frame portion after the irradiation field expansion. Thus, even when an irradiation field expansion is interposed during radiation emission, the trouble of radiographic images caused by high brightness can be reduced. Also in the radiation detecting device with large long time constant components of lag-behind parts (long-term lags), the above high brightness does not appear. This produces also the effects that a certain amount of waiting time until attenuation of high brightness is not needed, the burden of a patient is lightened, and the doctor's diagnosis is not obstructed.

Where a residual rate of component n of certain attenuation time constant $\tau_n$ is expressed as $\gamma_n$, and ratios of time constant component amounts are expressed as $\gamma_1:\gamma_2: \ldots :\gamma_n: \ldots : \gamma_{N-1}:\gamma_N$, the ratios can be regarded as constant before and after the irradiation field expansion. Therefore, for pixels common before and after the irradiation field expansion, pixel values based on the radiation detection signals in time of non-emission are divided for each attenuation time constant, using the ratio of time constant component amounts at an irradiation time before the irradiation field expansion and immediately before the time of non-emission, and each divided value is set as the above initial value (derived from the radiation detection signals at the time of non-emission due to the temporary stop); and for pixels in a portion newly added by the irradiation field expansion, pixel values based on the radiation detection signals in time of non-emission are divided for each attenuation time constant, using the same ratio of time constant component amounts as used for the above common pixels, and each divided value is set as the initial value; whereby, after the irradiation field expansion, the lag-behind parts are removed by the recursive computation based on the respective initial values, to obtain the corrected radiation detection signals. More particularly, the following measure is taken.

The recursive computation is carried out, after the above irradiation field expansion, for removing the lag-behind parts from the radiation detection signals, based on the following equations A-C:

$$X_k = Y_k - \Sigma_{n=1}^{N}[S_{nk}] \quad\quad\quad A$$

$$T_n = -\Delta t/\tau_n \quad\quad\quad B$$

$$S_{nk} = \exp(T_n) \cdot \{\alpha_n \cdot [1-\exp(T_n)] \cdot \exp(T_n) \cdot S_{n(k-1)}\} \quad\quad\quad C$$

where
  $\Delta t$: the sampling time interval;
  k: a subscript representing a k-th point of time in a sampling time series;
  $Y_k$: a radiation detection signal taken at the k-th sampling time;
  $X_k$: a corrected radiation detection signal with a lag-behind part removed from the signal $Y_k$;
  $X_{k-1}$: a signal $X_k$ taken at a preceding point of time;
  $S_{n(k-1)}$: an $S_{nk}$ at a preceding point of time;
  exp: an exponential function;
  N: the number of exponential functions with different time constants forming the impulse response;
  n: a subscript representing one of the exponential functions forming the impulse response;
  $\alpha_n$: an intensity of exponential function n; and
  $\tau_n$ an attenuation time constant of exponential function n;
to determine said initial values as in the following equations D and H, with a sampling point in time of emission before said irradiation field expansion and immediately before the time of non-emission expressed as k':

$$X_0=0, S_{n0}=\gamma_n \cdot Y_0 \quad\quad\quad D$$

$$\gamma_n = S_{nk'}/\Sigma_{n=1}^{N}[S_{nk'}] \quad\quad\quad H$$

where
  $\gamma_n$: residual rate of component n of certain attenuation time constant $\tau_n$;
  $Y_0$: lag signal value remaining at the radiation non-emission time serving as the base point for the recursive computation after said irradiation field expansion (radiation detection signal at the non-emission time); and
  $S_{nk'}$: $S_{nk}$ at sampling point k'; and to obtain the corrected radiation detection signals by removing the lag-behind parts based on said impulse response derived from said equations A-C with conditions of the initial values determined from said equations D and H.

In this case, the corrected, lag-free radiation detection signal $X_k$ is derived promptly from equations A-C constituting a compact recurrence formula after the irradiation field expansion noted above. Here, the above equations D and H are used to derive initial values from a ratio of time constant component amounts at the time of irradiation before the irradiation field expansion and immediately before the non-emission time (sampling point k').

EFFECTS OF THE INVENTION

With the radiographic apparatus and radiation detection signal processing method according to this invention, when a predetermined operation relating to radiographic imaging is interposed during radiation emission, the emission is stopped temporarily, and also the recursive computation is stopped temporarily, as in (B) noted above. With start of the predetermined operation, emission is started again, and the recursive computation also is started again, as in (C) noted above. Radiation detection signals at the time of non-emission due to the temporary stop are acquired as in (B), and a recursive computation is carried out based on the initial values derived from the radiation detection signals at the time of non-emission as in (C). Lag-behind parts can be removed from the radiation detection signals with increased accuracy while reducing the trouble of radiographic images caused by the predetermined operation relating to radiographic imaging interposed during radiation emission.

Block diagram showing an overall construction of a fluoroscopic apparatus according to an embodiment

FIG. 2

Plan view showing a construction of an FPD used in the apparatus according to the embodiment

FIG. 3

Schematic view showing a state of sampling X-ray detection signals during X-ray radiography by the apparatus according to the embodiment

FIG. 4

Flow chart showing a procedure of an X-ray detection signal processing method according to the embodiment

FIG. 5

Flow chart showing a recursive computation process for time lag removal before an irradiation field expansion in the X-ray detection signal processing method according to the embodiment

FIG. 6

Flow chart showing a recursive computation process for time lag removal after the irradiation field expansion in the X-ray detection signal processing method according to the embodiment

FIG. 7

Flow chart showing a procedure before and after the irradiation field expansion, irradiation and recursive computation according to the embodiment

FIG. 8

View showing, in a time series relationship, irradiation situations and images before and after the irradiation field expansion according to the embodiment

FIG. 9

View showing time lags corresponding to a state of radiation incidence

FIG. 10

View showing a time lag state with lags of radiography (time lags) superimposed on fluoroscopy

FIG. 11

View schematically showing images before and after an irradiation field expansion

FIG. 12

View showing, in a time series relationship, irradiation situations and images before and after the irradiation field expansion according to the prior art

DESCRIPTION OF REFERENCES

1 . . . X-ray tube
2 . . . FPD (flat panel X-ray detector)
3 . . . A/D converter
11 . . . time lag remover
12 . . . emission controller
13 . . . collimator
M . . . patient

BEST MODE FOR CARRYING OUT THE INVENTION

When an irradiation field expansion is interposed during an emission of radiation, typically X rays, the emission is stopped temporarily, and also the recursive computation is stopped temporarily, as in (B) noted hereinbefore. With start of a predetermined operation, emission is started again, and the recursive computation also is started again, as in (C) noted hereinbefore. X-ray detection signals at the time of non-emission due to the temporary stop as in (B) are acquired, and a recursive computation is carried out based on initial values derived from the X-ray detection signals at the time of non-emission as in (C). Thus, the object is fulfilled to remove lag-behind parts from the X-ray detection signals with increased accuracy while reducing the trouble of radiographic images caused by the predetermined operation relating to radiographic imaging, typically the irradiation field expansion, interposed during radiation emission.

EMBODIMENT

Figure 1:
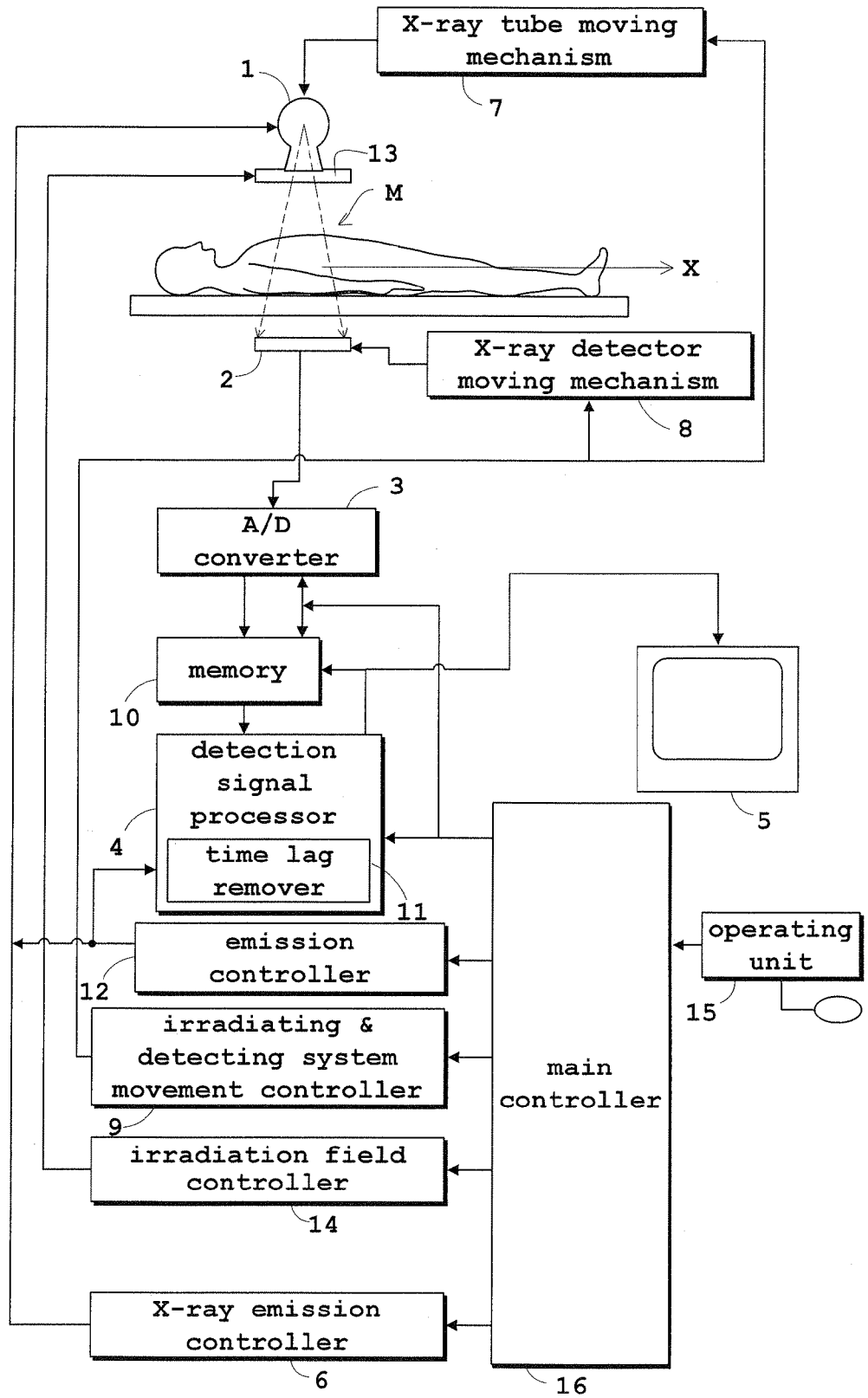
FIG. 1

An embodiment of this invention will be described with reference to the drawings. FIG. 1 is a block diagram showing an outline of a fluoroscopic apparatus according to the embodiment.

As shown in FIG. 1, the fluoroscopic apparatus includes an X-ray tube 1 for emitting X rays toward a patient M, an FPD 2 (flat panel X-ray detector) for detecting X rays transmitted through the patient M, an analog-to-digital converter 3 for digitizing X-ray detection signals taken from the FPD 2 at predetermined sampling time intervals $\Delta t$, a detection signal processor 4 for creating X-ray images based on X-ray detection signals outputted from the analog-to-digital converter 3, and an image monitor 5 for displaying the X-ray images acquired by the detection signal processor 4. That is, the apparatus in this embodiment is constructed to acquire X-ray images from the X-ray detection signals taken from the FPD 2 by the analog-to-digital converter 3 as the patient M is irradiated with X rays, and display the acquired X-ray images on the screen of the image monitor 5. Each component of this apparatus will particularly be described hereinafter. The X-ray tube 1 corresponds to the radiation emitting device in this invention. The FPD 2 corresponds to the radiation detecting device in this invention. The analog-to-digital converter 3 corresponds to the signal sampling device in this invention. The X-ray detection signals correspond to the radiation detection signals in this invention. The X-ray images correspond to the radiographic images in this invention.

The X-ray tube 1 and FPD 2 are opposed to each other across the patient M. Specifically, the X-ray tube 1 and FPD 2 are opposed to each other such that, in time of X-ray radiography, the X-ray tube 1 is controlled by an X-ray emission controller 6 to emit X rays in the form of a cone beam to the patient M, and at the same time, penetration X-ray images of the patient M produced by the X-ray emission are projected to an X-ray detecting surface of FPD 2.

The X-ray tube 1 and FPD 2 are movable back and forth along the patient M by an X-ray tube moving mechanism 7 and an X-ray detector moving mechanism 8, respectively. In moving the X-ray tube 1 and FPD 2, the X-ray tube moving mechanism 7 and X-ray detector moving mechanism 8 are controlled by an irradiating and detecting system movement controller 9 to move the X-ray tube 1 and FPD 2 together as opposed to each other, with the center of emission of X rays constantly in agreement with the center of the X-ray detecting surface of FPD 2. Movement of the X-ray tube 1 and FPD 2 results in variations in the position of the patient M irradiated with X rays, hence movement of a radiographed site.

Figure 2:
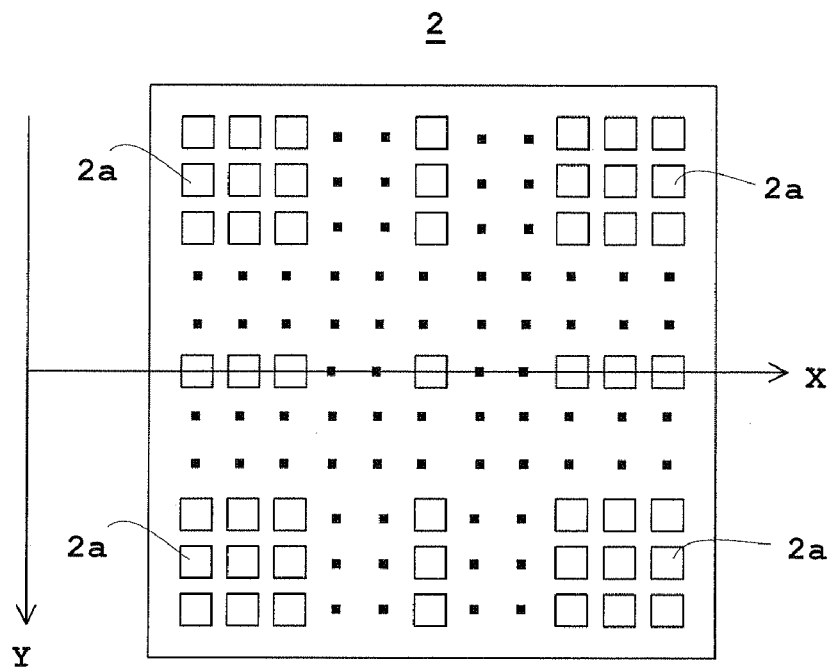

As shown in FIG. 2, the FPD 2 has numerous X-ray detecting elements 2a arranged longitudinally and transversely along the direction X of the body axis of patient M and the direction Y perpendicular to the body axis, on the X-ray detecting surface to which penetration X-ray images from the patient M are projected. For example, X-ray detecting elements 2a are arranged to form a matrix of 1536 by 1536 on the X-ray detecting surface about 30 cm long and 30 cm wide. Each X-ray detecting element 2a of FPD 2 corresponds to one pixel in an X-ray image created by the detection signal processor 4. Based on the X-ray detection signals taken from the FPD 2, the detection signal processor 4 creates an X-ray image corresponding to a penetration X-ray image projected to the X-ray detecting surface.

The analog-to-digital converter 3 continually takes X-ray detection signals for each X-ray image at sampling time intervals Δt, and stores the X-ray detection signals for X-ray image creation in a memory 10 disposed downstream of the converter 3. An operation for sampling (extracting) the X-ray detection signals is started before X-ray emission.

Figure 3:
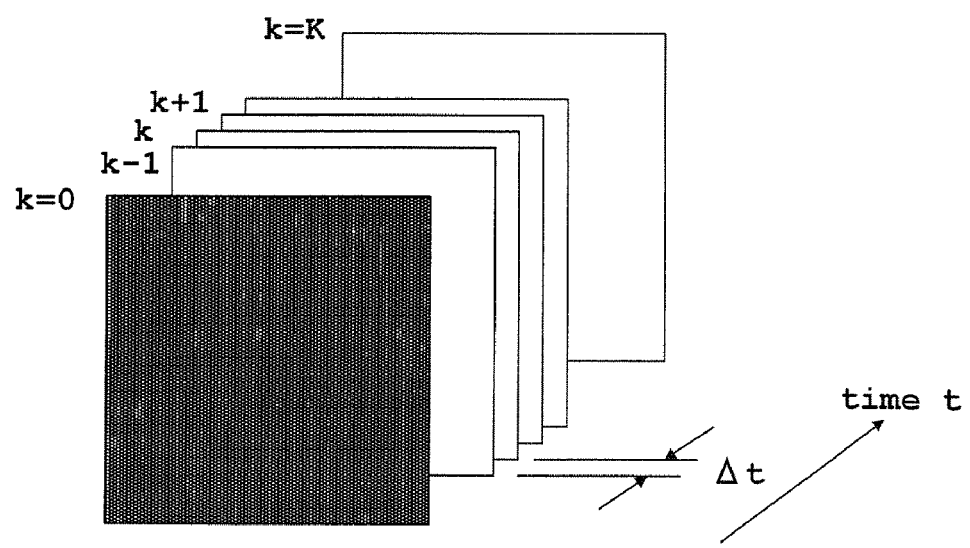

That is, as shown in FIG. 3, all X-ray detection signals for a penetration X-ray image are collected at each period between the sampling intervals Δt, and are successively stored in the memory 10. The sampling of X-ray detection signals by the analog-to-digital converter 3 before an emission of X rays may be started manually by the operator or automatically as interlocked with a command for X-ray emission.

As shown in FIG. 1, the fluoroscopic apparatus in this embodiment includes a time lag remover 11 for computing corrected radiation detection signals free from time lags, which are removed from the X-ray detection signals by a recursive computation process, an emission controller 12 for controlling timing of emission start and emission stop of the X-ray tube 1, and the irradiation stop, a collimator 13 for setting sizes of an irradiation field of X rays emitted from the X-ray tube 1, and an irradiation field controller 14 for controlling the collimator 13. The time lag remover 11 corresponds to the time lag removing device in this invention. The emission controller 12 corresponds to the emission control device in this invention. The collimator 13 corresponds to the irradiation field control device in this invention.

Figure 8:
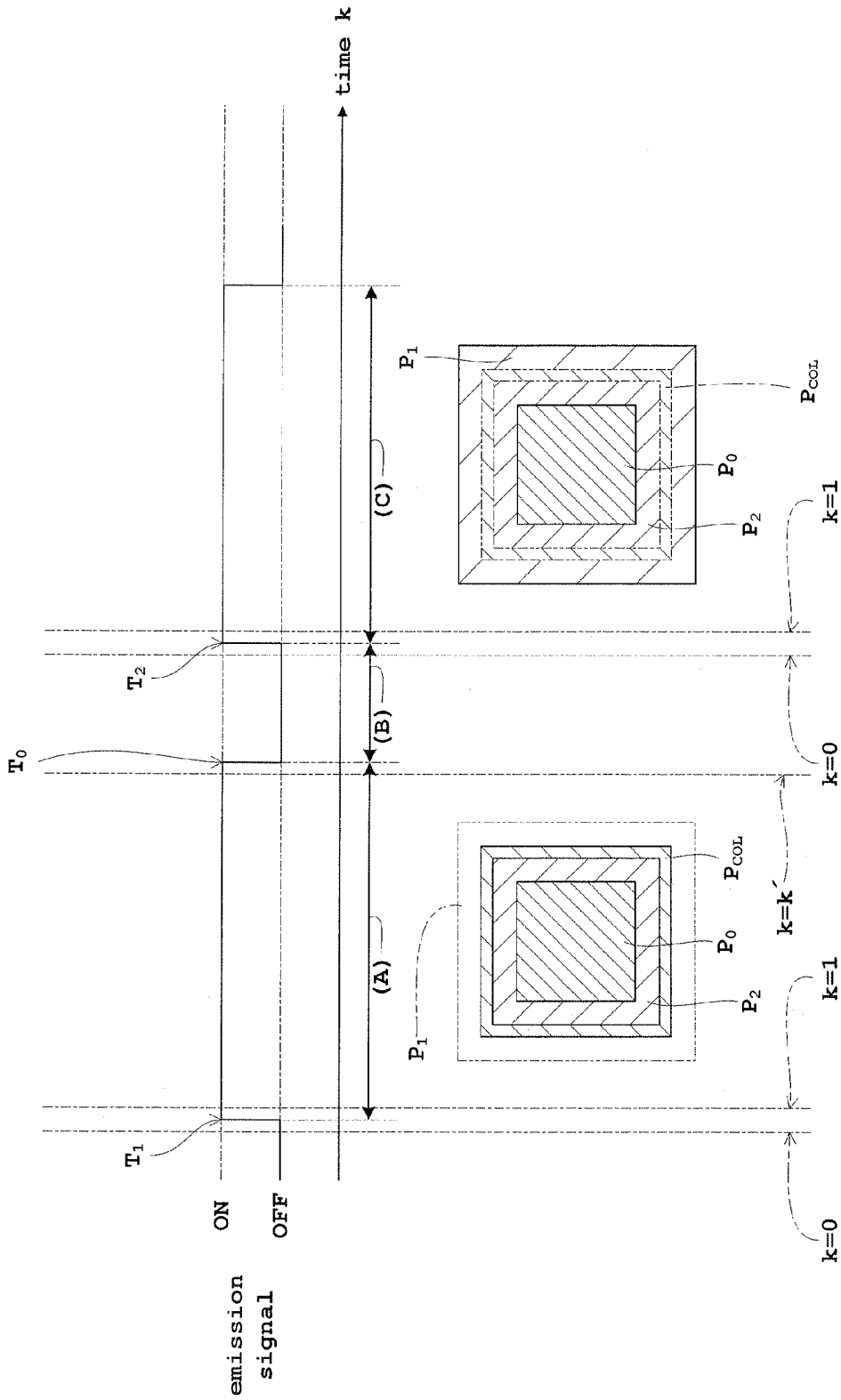

A time lag is included in each of the X-ray detection signals fetched at the sampling time intervals from the FPD 2. The time lag is removed from each X-ray detection signal by the above recursive computation process based on an assumption that the time lag included in each of the X-ray detection signals taken at the sampling time intervals from the FPD 2 is due to an impulse response formed of one or a plurality of exponential functions with different attenuation time constants. A process of removal from each X-ray detection signal is executed according to the following steps as shown in FIG. 8.

That is, (A) with the X-ray tube 1 caused to start emission (see a shift from OFF to ON at $T_1$ in FIG. 8) by the emission controller 12 which controls the timing of emission start and emission stop of the X-ray tube 1, the time lag remover 11 removes lag-behind parts by recursive computation to obtain corrected X-ray detection signals. And, (B) on an instruction for a predetermined operation relating to radiation imaging (an irradiation field expansion in this embodiment), the emission controller 12 stops the emission temporarily, the time lag remover 11 stops the recursive computation temporarily (see $T_0$ and sampling point k' in FIG. 8), and the analog-to-digital converter 3 acquires X-ray detection signals in time of non-irradiation with the temporary stop of the X-ray tube 1. Further, (C) with start of the above predetermined operation (irradiation field expansion), the emission controller 12 starts emission again, and the time lag remover 11 starts the recursive computation again (see a shift from OFF to ON at $T_2$ in FIG. 8) based on initial values derived from the X-ray detection signals in time of non-emission (see $T_0$-$T_2$ in FIG. 8).

Figure 9:
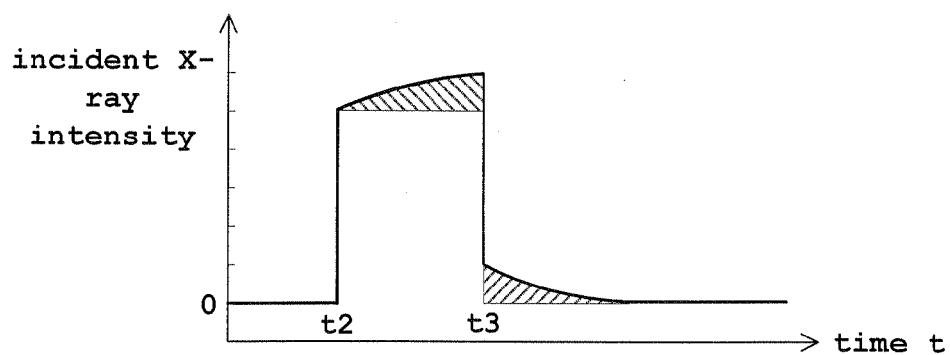

With the FPD 2, an X-ray detection signal generated at each point of time, as shown in FIG. 9, includes signals corresponding to preceding X-ray emissions and remaining as a lag-behind part (see a hatched part in FIG. 9). The time lag remover 11 removes this lag-behind part to produce a corrected, lag-free X-ray detection signal. Based on such lag-free X-ray detection signals, the detection signal processor 4 creates an X-ray image corresponding to a penetration X-ray image projected to the X-ray detecting surface. In this embodiment, before the predetermined operation (irradiation field expansion), the time lag remover 11 removes the lag-behind parts by recursive computation, and an X-ray image is acquired from the corrected X-ray detection signals obtained. After the predetermined operation (irradiation field expansion), the time lag remover 11 removes the lag-behind parts by recursive computation based on the initial values noted above, and an X-ray image is acquired from the corrected X-ray detection signals obtained.

Specifically, the time lag remover 11 performs a recursive computation process for removing a lag-behind part from each X-ray detection signal, before the predetermined operation (irradiation field expansion), by using the following equations A-C:

$$X_k = Y_k - \Sigma_{n=1}^{N}[S_{nk}] \quad\quad\quad A$$

$$T_n = -\Delta t / \tau_n \quad\quad\quad B$$

$$S_{nk} = \exp(T_n) \cdot \{\alpha_n \cdot [1 - \exp(T_n)] \cdot \exp(T_n) \cdot S_{n(k-1)}\} \quad\quad\quad C$$

where

Δt: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n.

The second term et seq. at the right side in equation A, i.e. "$S_{nk} = \exp(T_n) \cdot \{\alpha_n \cdot [1 - \exp(T_n)] \cdot \exp(T_n) \cdot S_{n(k-1)}\}$" in equation C, corresponds to the lag-behind part. Thus, the apparatus in this embodiment derives the corrected, lag-free X-ray detection signal $X_k$ promptly from equations A-C constituting a compact recurrence formula before the predetermined operation (irradiation field expansion) noted above.

Here, it is time k=0 that serves as the base point for the recursive computation, i.e. the X-ray non-emission time for the first frame. $X_k$ and $S_{nk}$ at the time of k=0, i.e. initial values, when carrying out the recursive computation, are determined as in the following equation D:

$$X_0=0, S_{n0}=\gamma_n \cdot Y_0 \qquad D$$

where $\gamma_n$: residual rate of component n of certain attenuation time constant $\tau_n$, and $Y_0$: lag signal value remaining at the X-ray non-emission time serving as the base point for the recursive computation.

Figure 10:
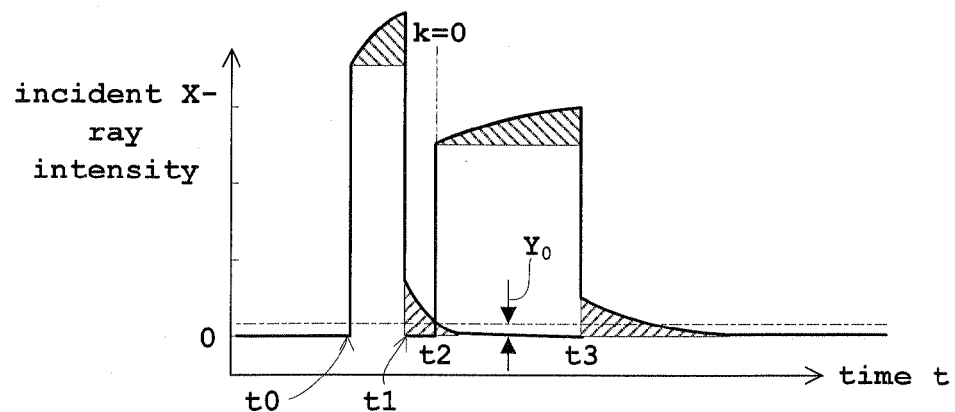

As shown in FIG. 10, for example, when a lag of the radiography in time t0-t1 is superimposed on fluoroscopy, a residual lag (lag signal value) due to a lag-behind part generated by the radiography in time t0-t1 exists even at the X-ray non-emission time (see k=0 in FIG. 10) which is the base point for the recursive computation. That is, the initial value $Y_0$ of X-ray detection signal $Y_k$ is not 0 even at the X-ray non-emission time.

Then, initial values for the recursive computation are set according to equation D, i.e. $X_0=0$, $S_{n0}=\gamma_n \cdot Y_0$ ($Y_0$: lag signal value remaining at the X-ray non-emission time serving as the base point for the recursive computation). A corrected X-ray detection signal $X_k$ is obtained by removing the lag-behind part based on the impulse response derived from equations A-C with conditions of the initial values determined from equation D.

On the other hand, the time lag remover 11 carries out a recursive computation process for removing a lag-behind part from each X-ray detection signal also after the predetermined operation (i.e. irradiation field expansion) noted above, using equations A-C. In equations A-C, the same equations as the recursive computation before the irradiation field expansion are used. For sampling time k here, a setting is made as follows, without using the sampling time before the irradiation field expansion. That is, in the shift from the time of non-emission due to the temporary stop (see $T_0$-$T_2$ in FIG. 8) to the resumption of emission and recursive computation accompanying the start of irradiation field expansion (see the shift from OFF to ON at $T_2$ in FIG. 8), a sampling time for a non-emission immediately preceding the resumption is set to k=0, and a sampling time for an emission immediately following the resumption is set to k=1. Thus, corrected, lag-free X-ray detection signal $X_k$ is derived promptly from equations A-C constituting a compact recurrence formula, also after the irradiation field expansion.

Here, initial values are derived from a ratio of time constant component amounts at the time of irradiation before the irradiation field expansion and immediately before the non-emission time (sampling point k'). Specifically, $X_k$ at the time of k=0 which is the sampling time during non-emission immediately before the resumption, i.e. initial value, is determined as in equation D, and residual rate $\gamma_n$ in equation D is determined as in the following equation H using $S'_{nk}$ at the time of sampling k=k' at the irradiation time before the irradiation field expansion and immediately before the non-emission time.

$$\gamma_n = S_{nk'}/\Sigma_{n=1}^{N}[S_{nk'}] \qquad H$$

where $\gamma_n$: residual rate of component n of certain attenuation time constant $\tau_n$;

$Y_0$: lag signal value remaining at the X-ray non-emission time serving as the base point for the recursive computation after the above irradiation field expansion (X-ray detection signal at the non-emission time); and $S_{nk'}$: $S_{nk}$ at sampling point k'.

In equation D, the same equation as the initial value before the irradiation field expansion noted above is used.

With the apparatus in this embodiment, the analog-to-digital converter 3, detection signal processor 4, X-ray emission controller 6, irradiating and detecting system movement controller 9, time lag remover 11, emission controller 12 and irradiation field controller 14 are operable on instructions (e.g. an instruction for irradiation field expansion) and data inputted from an operating unit 15 or on various commands outputted from a main controller 16 with progress of X-ray radiography.

Figure 4:
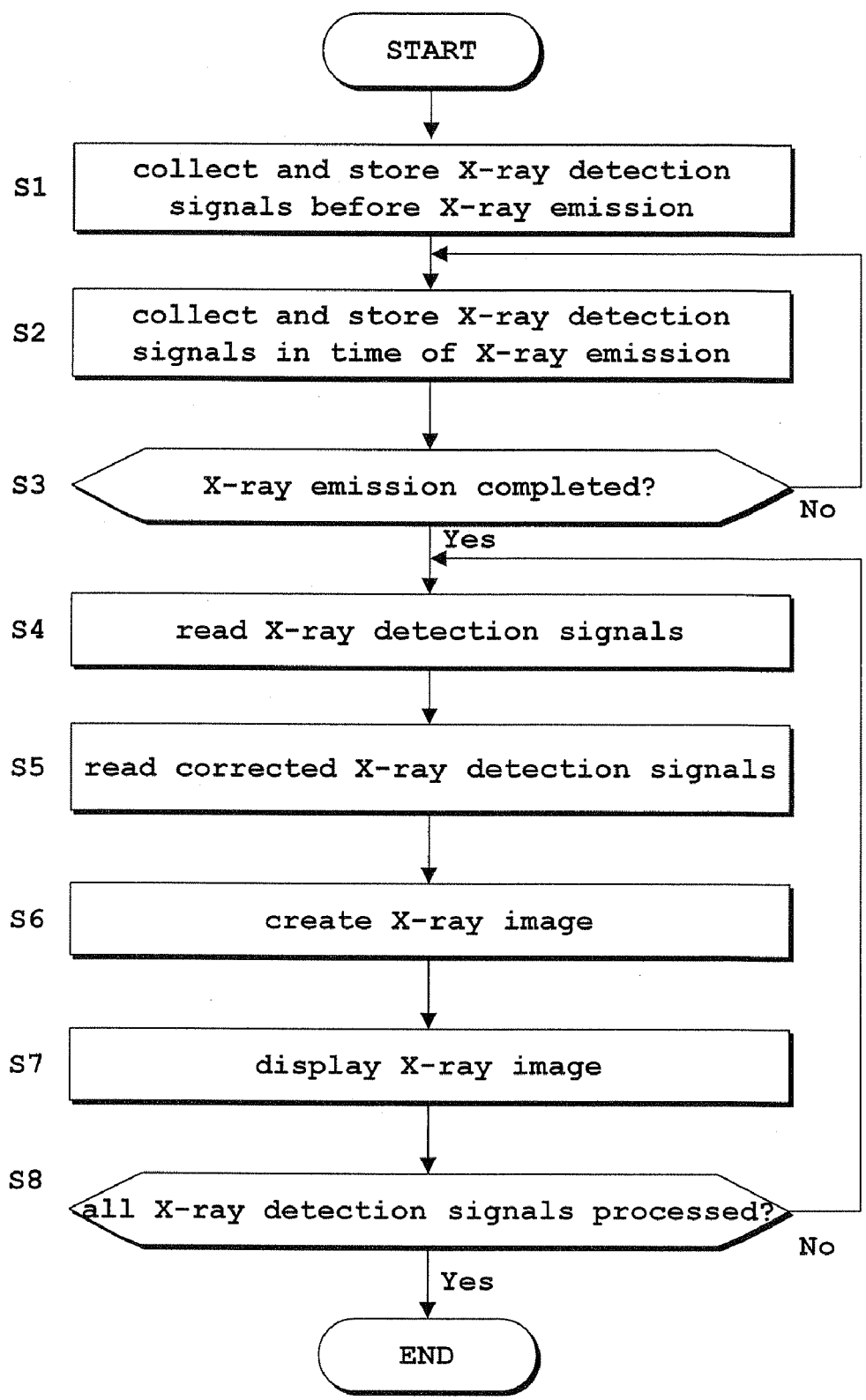

Next, an operation for performing X-ray radiography with the apparatus in this embodiment will particularly be described with reference to the drawings. FIG. 4 is a flow chart showing a procedure of an X-ray detection signal processing method according to the embodiment. The radiography herein includes previous radiography as shown in FIG. 10, and current fluoroscopy or radiography.

[Step S1] The analog-to-digital converter 3 starts taking X-ray detection signals $Y_k$ for one X-ray image from the FPD 2 at each period between the sampling time intervals $\Delta t$ (=1/30 second) before X-ray emission. The X-ray detection signals taken are stored in the memory 10.

[Step S2] In parallel with a continuous or intermittent X-ray emission to the patient M initiated by the operator, the analog-to-digital converter 3 continues taking X-ray detection signals $Y_k$ for one X-ray image at each period between the sampling time intervals $\Delta t$ and storing the signals in the memory 10.

[Step S3] When the X-ray emission is completed, the operation proceeds to step S4. When the X-ray emission is uncompleted, the operation returns to step S2.

[Step S4] X-ray detection signals $Y_k$ for one X-ray image collected in one sampling sequence are read from the memory 10.

[Step S5] The time lag remover 11 performs the recursive computation based on the equations A-C, and derives corrected X-ray detection signals $Y_k$, i.e. pixel values, with lag-behind parts removed from the respective X-ray detection signals $Y_k$.

[Step S6] The detection signal processor 4 creates an X-ray image based on the corrected X-ray detection signals $X_k$ for one sampling sequence (for one X-ray image).

[Step S7] The X-ray image created is displayed on the image monitor 5.

[Step S8] When unprocessed X-ray detection signals $Y_k$ remain in the memory 10, the operation returns to step S4. When no unprocessed X-ray detection signals remain, the X-ray radiography is ended.

With the apparatus in this embodiment, the time lag remover 11 computes the corrected X-ray detection signals $X_k$ corresponding to the X-ray detection signals $Y_k$ for one X-ray image, and the detection signal processor 4 creates an X-ray image, both at each period between the sampling time intervals $\Delta t$ (=1/30 second). That is, the apparatus is constructed also for creating X-ray images one after another at a rate of about 30 images per second, and displaying the created X-ray images continuously. It is thus possible to perform a dynamic display of X-ray images.

Figure 5:
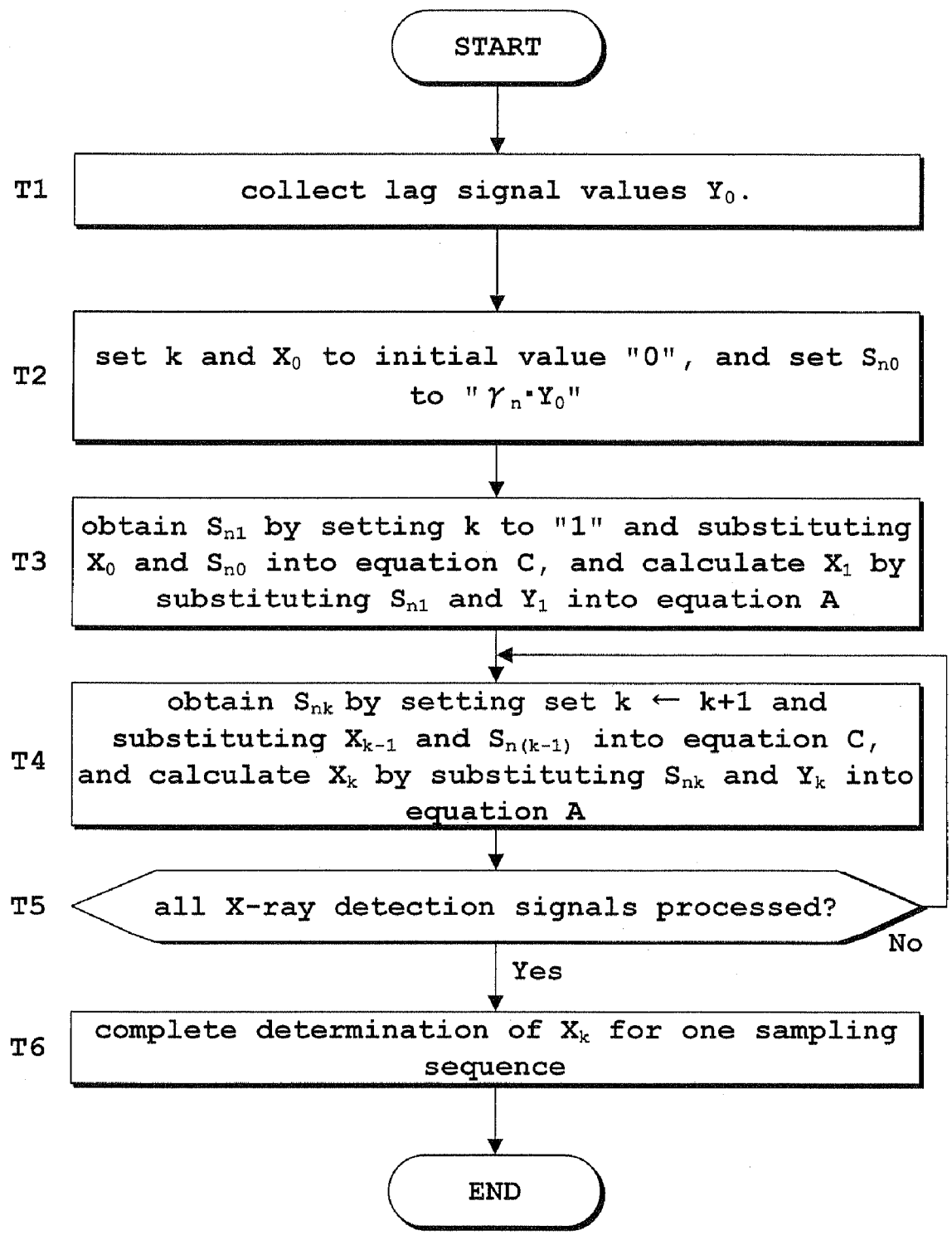
Figure 6:
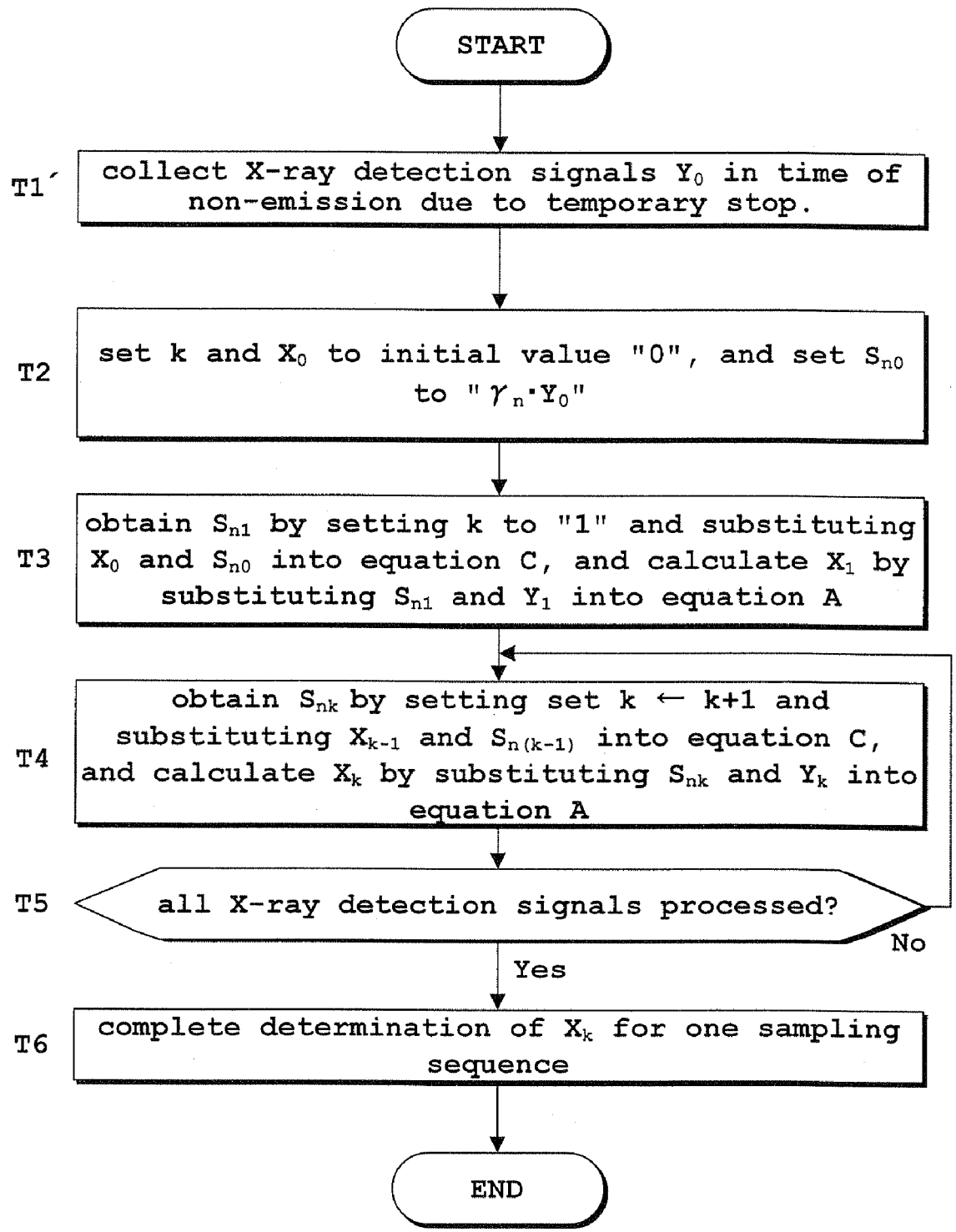
Figure 7:
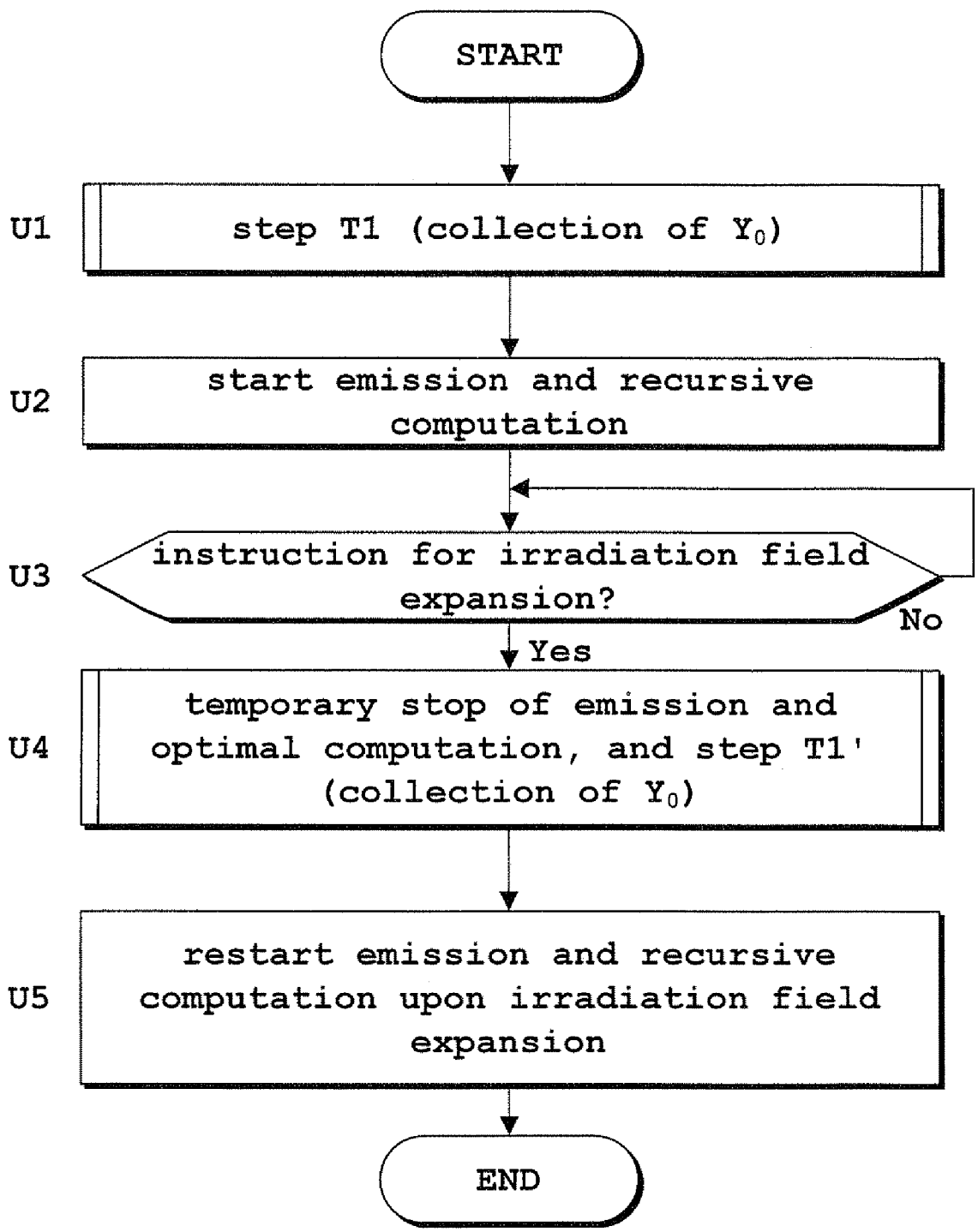

Next, the process of recursive computation carried out in step S5 in FIG. 4 by the time lag remover 11 will be described with reference to the flow charts of FIGS. 5 and 6. Procedures of irradiation and recursive computation before and after the irradiation field expansion, including collection of X-ray detection signals $Y_k$ (i.e. $Y_0$) at the time of k=0 in steps T1 and T1' in FIGS. 5 and 6, will be described with reference to the flow charts of FIGS. 7 and 8. FIG. 5 is a flow chart showing a recursive computation process for time lag removal before an irradiation field expansion in the radiation detection signal processing method in this embodiment. FIG. 6 is a flow chart showing a recursive computation process for time lag removal after the irradiation field expansion in the X-ray detection signal processing method according to the embodiment. FIG. 7 is a flow chart showing a procedure before and after the irradiation field expansion, irradiation and recursive computation process according to the embodiment. FIG. 8 is a view showing, in a time series relationship, irradiation situations and images before and after the irradiation field expansion according to the embodiment.

[Step U1] Residual lags (lag signal values) due to lag-behind parts generated in past radiography are collected at the time of non-emission before an irradiation field expansion. At this time, k=0 is set. The process of collecting X-ray detection signals $Y_k$ (i.e. $Y_0$) at the time of k=0 is also step T1 in FIG. 5, and will be described later at step T1.

[Step U2] With emission started (see the shift from OFF to ON at $T_1$ in FIG. 8), the lag-behind parts are removed by recursive computation to obtain corrected X-ray detection signals. A more specific process will be described later at steps T1-T6 in FIG. 5.

[Step U3] When an instruction for irradiation field expansion is inputted from the operating unit 15 (FIG. 1), the operation proceeds to step U4. Otherwise, the operation stands by at step U3.

[Step U4] Upon instruction for irradiation field expansion, the emission is stopped temporarily, and the recursive computation is stopped temporarily (see $T_0$ and sampling point k' in FIG. 8). X-ray detection signals in time of non-emission due to the temporary stop are collected. The time immediately preceding the input of the instruction for irradiation field expansion is a time of emission before an irradiation field expansion, and is immediately before the time of non-emission. The sampling point at this time is regarded as k=k' as noted hereinbefore. On the other hand, the time immediately after the input of the instruction for irradiation field expansion is a time of non-emission due to the temporary stop. At this time, k=0 is set. The process of collecting X-ray detection signals $Y_k$ (i.e. $Y_0$) at the time of k=0 is also step T1' in FIG. 6, and will be described later at step T1'.

[Step U5] With start of an irradiation field expansion, emission is started again, and the recursive computation is also started again (see the shift from OFF to ON at $T_2$ in FIG. 8). Thus, after the irradiation field expansion, lag-behind parts are removed to obtain corrected X-ray detection signals, by a recursive computation based on the initial values derived from the X-ray detection signals acquired in time of non-emission (see $T_0$-$T_2$ in FIG. 8). A the more specific process will be described later at steps T1' and T2-T6 in FIG. 5.

Next, a specific process of recursive computation including the collection of X-ray detection signals $Y_k$ (i.e. $Y_0$) at the time of k=0 in steps T1 and T1' will be described. First, a process before the irradiation field expansion will be described with reference to FIG. 5, and then a process after the irradiation field expansion will be described with reference to FIG. 6.

[Step T1] Residual lags (lag signal values) due to lag-behind parts generated in past radiography are collected. Specifically, in the first frame, the analog-to-digital converter 3 fetches X-ray detection signals $Y_0$ for one X-ray image from the FPD 2. These X-ray detection signals $Y_0$ are also lag signal value $Y_0$ remaining at the time of X-ray non-emission serving as the base point for recursive computation.

[Step T2] A setting k=0 is made, and $X_0$=0 in equation A is set as initial value. On the other hand, by substituting lag signal value $Y_0$ acquired at step T1 into equation D, $S_{n0}$ in equation C is calculated. It is preferred to set residual rate $\gamma_n$ of component n of certain attenuation time constant $\tau_n$ before the irradiation field expansion to satisfy the condition of equation E.

That is, it is preferred to set it to satisfy;

$$\Sigma_{n=1}^{N}[\gamma_n] \leq 1, 0 \leq \gamma_n \qquad \text{E}$$

where $\Sigma_{n=1}^{N}[\gamma_n]$: total of residual rates $\gamma_n$ of component n.

When the total of residual rates $\gamma_n$ of components n exceeds 1, the lag-behind parts will be removed excessively. Conversely, when the total of residual rates $\gamma_n$ of components n is a negative value, there is a possibility that the lag-behind parts are added. Then, the lag-behind parts can be removed neither too much nor too little by making the total of residual rates $\gamma_n$ of components n 0 or more and 1 or less, and making residual rates $\gamma_n$ 0 or more. Equation E may be the following equation E' or the following equation E".

That is, when equation E is the following equation E', equation E is set to satisfy the condition of;

$$\Sigma_{n=1}^{N}[\gamma_n] = 1 \qquad \text{E'},$$

and each residual rate $\gamma_n$ is set to satisfy the condition of equation F:

$$\gamma_1 = \gamma_2 = \cdots = \gamma_n = \cdots = \gamma_{N-1} = \gamma_N \qquad \text{F}$$

Equation F is substituted into equation E' to make $N \cdot \gamma_N = 1$. Therefore, each residual rate $\gamma_n$ becomes $\gamma_N = 1/N$, and each residual rate $\gamma_n$ is equally distributed with number N of exponential functions (with different time constants constituting an impulse response). Thus, equation D is expressed by the following equation D' by substituting $\gamma_N = 1/N$ into $S_{n0} = \gamma_n \cdot Y_0$ of equation D.

That is, equation D is expressed by;

$$S_{n0} = Y_0/N \qquad \text{D'}.$$

When the number of exponential functions is three (N=3), $S_{10}$, $S_{20}$ and $S_{30}$ are all set to $Y_0/3$ according to equation D.

When equation E is the following equation E", equation E is set to satisfy the condition of;

$$\Sigma_{n=1}^{N}[\gamma_n] < 1 \qquad \text{E"},$$

and residual rate $\gamma_M$ in component m of certain attenuation time constant $\tau_m$ and other residual rate $\gamma_N$ to satisfy equation G:

$$0 < \gamma_M < 1, \gamma_N = 0 \qquad \text{G}$$

When the number of exponential functions is three (N=3), residual rate $\gamma_2$ in component 2 of attenuation time constant $\tau_2$ satisfies $0 < \gamma_2 < 1$ (e.g. $\gamma_2 = 0.1$) and the other residual rate satisfies $\gamma_1 = \gamma_3 = 0$, $S_{10}$ and $S_{30}$ are set to 0 according to equation G, and $S_{20}$ is set to $\gamma_2 \cdot Y_0$ (e.g. $\gamma_2 = 0.1$) according to equation G.

[Step T3] In equations A and C, k=1 is set. $S_{11}$, $S_{21}$ and $S_{31}$ are derived from equation C, i.e. $S_{n1} = \exp(T_1) \cdot \{\alpha_1 \cdot [1 - \exp(T_1)] \cdot \exp(T_1) \cdot S_{n0}\}$. Further, a corrected X-ray detection signal $X_1$ is obtained by substituting $S_{11}$, $S_{21}$ and $S_{31}$ derived and X-ray detection signal $Y_1$ into equation A.

[Step T4] After incrementing k by 1 (k=k+1) in equations A and C, $X_{k-1}$ of a preceding time is substituted into equation C, thereby obtaining $S_{1k}$, $S_{2k}$ and $S_{3k}$. Further, corrected X-ray detection signal $X_k$ is obtained by substituting $S_{1k}$, $S_{2k}$ and $S_{3k}$ derived and X-ray detection signal $Y_k$ into equation A.

[Step T5] When there remain unprocessed X-ray detection signals $Y_k$, the operation returns to step T4.

When no unprocessed X-ray detection signals $Y_k$ remain, the operation proceeds to the next step T6.

[Step T6] Corrected X-ray detection signals $X_k$ for one sampling sequence (for one X-ray image) are obtained to complete the recursive computation for the one sampling sequence before the irradiation field expansion.

[Step T1'] In time of non-emission due to the temporary stop following the instruction for irradiation field expansion, residual lags (lag signal values) are collected as in step T1 before the irradiation field expansion. These residual lags are also X-ray detection signals $Y_0$ for one X-ray image at the time of the non-emission with the setting k=0. The one X-ray image acquired with this k=0 is the image $P_1$ after the irradiation field expansion, including the outer frame portion $P_2$ after the irradiation field expansion.

[Step T2] Since this is the same as step T2 before the irradiation expansion, its description is omitted. However, residual rate $\gamma_n$ is not derived from equation E used before the irradiation field expansion, but is derived from the above equation H.

When the ratios of time constant component amounts are expressed as $\gamma_1:\gamma_2:\ldots:\gamma_n:\ldots:\gamma_{N-1}:\gamma_N$, the ratios can be regarded as invariable before and after the irradiation field expansion. Therefore, for pixels common before and after the irradiation field expansion, pixel values based on the X-ray detection signals at the time of non-emission (i.e. $Y_0$ acquired in step T1') are divided for each attenuation time constant, using the ratio of time constant component amounts expressed by equation H using $S'_{nk}$ at the time of sampling k=k' during the emission before the irradiation field expansion and immediately before the time of non-emission. Each divided value is set, using equation D, as the initial value noted hereinbefore (obtained from the X-ray detection signals at the time of non-emission due to the temporary stop).

On the other hand, for pixels in the portion newly added by the irradiation field expansion, pixel values based on the X-ray detection signals at the time of non-emission (i.e. $Y_0$ acquired in step T1') are divided for each attenuation time constant, using the same ratio of time constant component amounts as used for the above common pixels. Each divided value is set as the initial value noted hereinbefore (obtained from the X-ray detection signals at the time of non-emission due to the temporary stop).

Where, for example, the number of exponential functions is three (N=3), and $\gamma_1=0.5$, $\gamma_2=0.3$, $\gamma_3=0.2$ and the ratio of $\gamma_1:\gamma_2:\gamma_3=0.5:0.3:0.2$ are constant, the pixel values based on X-ray detection signals $Y_0$ may be divided for each attenuation time constant by multiplying X-ray detection signals $Y_0$ by 0.5 as lag-behind parts for $\gamma_1$, multiplying X-ray detection signals $Y_0$ by 0.3 as lag-behind parts for $\gamma_2$, and multiplying X-ray detection signals $Y_0$ by 0.2 as lag-behind parts for $\gamma_3$.

To summarize the above, in this embodiment, whether common pixels or pixels of the portion newly added by the irradiation field expansion, pixel values based on X-ray detection signals $Y_0$ are divided for each attenuation time constant, by multiplying X-ray detection signals $Y_0$, pixel by pixel, by residual rates $\gamma_1, \gamma_2, \ldots, \gamma_n, \ldots, \gamma_{N-1}$ and $\gamma_N$, as in equation D noted hereinbefore. That is, equation D becomes $S_{n0}(i, j)=\gamma_n \cdot Y_0(i,j)$. Here, the coordinates in the body axis direction X and body transverse direction Y are set to (i, j). When binning is carried out to add pixels after the irradiation field expansion, X-ray detection signals $Y_0$ may be multiplied by each of residual rates $\gamma_1, \gamma_2, \ldots, \gamma_n, \ldots, \gamma_{N-1}$ and $\gamma_N$, with the pixels binned are added.

For $S'_{nk}$ at the time of k=k', the value of one pixel in image $P_0$ before the irradiation field expansion may be selected. In order to improve accuracy, it is possible use an average value of all the pixels in image $P_0$ before the irradiation field expansion.

[Step T3] This is the same as step T3 before the irradiation expansion, and its description is omitted.

[Step T4] This is the same as step T4 before the irradiation expansion, and its description is omitted.

[Step T5] This is the same as step T5 before the irradiation expansion, and its description is omitted.

[Step T6] This is the same as step T6 before the irradiation expansion, and its description is omitted. Through steps T1' and T2-T6, the recursive computation for one radiographic operation after the irradiation field expansion is completed.

According to the fluoroscopic apparatus in this embodiment, as described above, when the predetermined operation noted hereinbefore (i.e. an irradiation field expansion) is interposed during X-ray emission, the emission is stopped temporarily, and also the recursive computation is stopped temporarily, as in (B) noted hereinbefore. With start of the predetermined operation (irradiation field expansion), emission is started again, and the recursive computation also is started again, as in (C) noted hereinbefore. Therefore, in (C), emission and recursive computation can be carried out after the predetermined operation (irradiation field expansion) as before the predetermined operation (irradiation field expansion). With the temporary stop in (B), the emission and recursive computation before the predetermined operation (irradiation field expansion) do not impart influence on the data after the predetermined operation (irradiation field expansion). On the other hand, the analog-to-digital converter 3 acquires X-ray detection signals at the time of non-emission due to the temporary stop as in (B), and a recursive computation is carried out based on initial values derived from the X-ray detection signals at the time of non-emission as in (C). Even if the predetermined operation noted hereinbefore (irradiation field expansion) is interposed during X-ray emission, lag-behind parts can be removed from the X-ray detection signals with increased accuracy while reducing the trouble of X-ray images caused by the predetermined operation (irradiation field expansion) relating to X-ray imaging interposed during X-ray emission.

Figure 11:
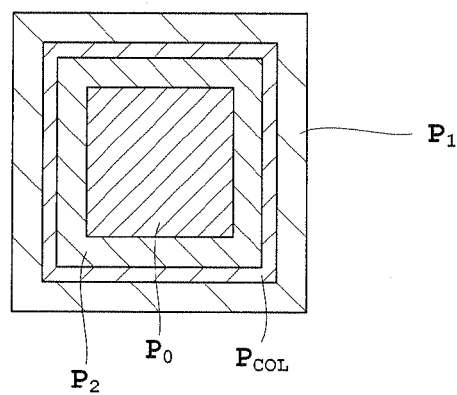

Before an irradiation field expansion in particular, the following effect is produced when the size of the irradiation field is changed to be larger (e.g. to 13 inches) than an image to be subjected to the recursive computation (e.g. 12 inches) and smaller than an image to be subjected to the recursive computation after the irradiation field expansion (e.g. 15 inches). Before the irradiation field expansion, an image larger than an image to be subjected to the recursive computation and smaller than an image to be subjected to the recursive computation after the irradiation field expansion is, as shown in FIGS. 8 and 11, an image excluding image $P_{COL}$ of the portion corresponding to the collimator 13 from image $P_1$ after the irradiation field expansion (i.e. the image to be subjected to the recursive computation after the irradiation field expansion), and also an image combining image $P_0$ before the irradiation field expansion (i.e. the image to be subjected to the recursive computation before the irradiation field expansion) and the outer frame portion $P_2$ present between image $P_0$ before the irradiation field expansion and image $P_{COL}$ of the portion corresponding to the collimator 13.

In the prior art, the outer frame portion $P_2$ not subjected to the recursive computation is left in the irradiated state before and after an irradiation field expansion. With the temporary stop in (B) noted above, the emission and recursive computation before the irradiation field expansion do not impart influence on the data of the outer frame portion $P_2$ after the irradiation field expansion. On the other hand, X-ray detection signals at the time of non-emission due to the temporary stop are acquired as in (B), and the recursive computation is carried out based on initial values derived from the X-ray detection signals at the time of non-emission as in (C). Thus, lag-behind parts due to the recursive computation can be removed with the above initial values with increased accuracy also for the outer frame portion $P_2$ after the irradiation field expansion.

Thus, even when an irradiation field expansion is interposed during X-ray emission, the trouble of X-ray images caused by high brightness can be reduced. Also in the FPD 2 with large long time constant components of lag-behind parts (long-term lags), the above high brightness does not appear. This produces also the effects that a certain amount of waiting time until attenuation of high brightness is not needed, the burden of the patient M is lightened, and the doctor's diagnosis is not obstructed.

This invention is not limited to the foregoing embodiment, but may be modified as follows:

(1) The foregoing embodiment employs an FPD as the radiation detecting device. This invention is applicable also to an apparatus having a radiation detecting device other than an FPD that causes time lags in X-ray detection signals.

(2) While the apparatus in the foregoing embodiment is a fluoroscopic apparatus, this invention is applicable also to an apparatus other than the fluoroscopic apparatus, such as an X-ray CT apparatus.

(3) The apparatus in the foregoing embodiment is designed for medical use. This invention is applicable not only to such medical apparatus but also to an apparatus for industrial use such as a nondestructive inspecting apparatus.

(4) The apparatus in the foregoing embodiment uses X rays as radiation. This invention is applicable also to an apparatus using radiation other than X rays (e.g. gamma rays).

(5) In the foregoing embodiment. initial values are determined from equation D. Before an irradiation field expansion, in the absence of residual lags (lag signal values) due to lag-behind parts generated in the radiography at time t0-t1 as shown in FIG. 10, during the X-ray non-emission time which is the base point for recursive computation, $X_0=0$ of equation A and $S_{n0}=0$ of equation C may all be set as initial values before X-ray emission.

(6) In the foregoing embodiment, corrected X-ray detection signals are obtained by removing lag-behind parts based on the impulse response derived from equations A-C. As described with relation to the technique of Patent Document 2 (Unexamined Patent Publication No. 2004-242741), lag-behind parts may be removed based on the impulse response derived from equations a-c.

(7) In the foregoing embodiment, the predetermined operation relating to radiation imaging is an irradiation field expansion. The invention is not limited to the irradiation field expansion, but is applicable also to any other operation relating to radiation imaging.

INDUSTRIAL UTILITY

As described above, this invention is suitable for a radiographic apparatus having a flat panel X-ray detector (FPD).

The invention claimed is:

1. A radiographic apparatus for obtaining radiographic images based on radiation detection signals, comprising a radiation emitting device for emitting radiation toward an object under examination, a radiation detecting device for detecting radiation transmitted through the object under examination, and a signal sampling device for taking radiation detection signals from the radiation detecting device at predetermined sampling time intervals, said apparatus being constructed to obtain radiographic images based on the radiation detection signals outputted from the radiation detecting device at the predetermined sampling time intervals as radiation is emitted to the object under examination, said apparatus further comprising a time lag removing device for removing lag-behind parts from the radiation detection signals by a recursive computation, on an assumption that a lag-behind part included in each of said radiation detection signals taken at the predetermined sampling time intervals is due to an impulse response formed of a single or a plurality of exponential functions with different attenuation time constants; and an emission control device for controlling timing of emission start and emission stop of said radiation emitting device; characterized in that (A) in a state where the emission control device having caused the radiation emitting device to start emission, said time lag removing device removes the lag-behind parts by recursive computation to obtain corrected radiation detection signals, (B) in response to an instruction for a predetermined operation relating to radiographic imaging, the emission control device causes said radiation emitting device to stop the emission temporarily, the time lag removing device stops the recursive computation temporarily, and said signal sampling device acquires radiation detection signals in time of non-emission due to the temporary stop of the radiation emitting device, and (C) with start of said predetermined operation, the emission control device causes the radiation emitting device to start emission again, and the time lag removing device starts the recursive computation again based on initial values derived from the radiation detection signals in time of said non-emission.

2. A radiographic apparatus as defined in claim 1, characterized in that said time lag removing device is arranged to carry out the recursive computation, before said predetermined operation, for removing the lag-behind parts from the radiation detection signals, based on the following equations A-C:

$$Xk = Yk - \Sigma n = 1 N[Snk] \qquad \text{A}$$

$$Tn = -\Delta t / \tau n \qquad \text{B}$$

$$Snk = \exp(Tn) \cdot \{\alpha n \cdot [1 - \exp(Tn)] \cdot \exp(Tn) \cdot Sn(k-1)\} \qquad \text{C}$$

where $\Delta t$: the sampling time interval;

k: a subscript representing a k-th point of time in a sampling time series;

Yk: a radiation detection signal taken at the k-th sampling time;

Xk: a corrected radiation detection signal with a lag-behind part removed from the signal Yk;

Xk−1: a signal Xk taken at a preceding point of time;

Sn(k−1): an Snk at a preceding point of time;

exp: an exponential function;

N: the number of exponential functions with different time constants forming the impulse response;

n: a subscript representing one of the exponential functions forming the impulse response;

αn: an intensity of exponential function n; and

τn: an attenuation time constant of exponential function n;

to determine the initial values for the recursive computation as in the following equation D:

$$X0 = 0, Sn0 = \gamma n \cdot Y0 \qquad \text{D}$$

where γn: residual rate of component n of certain attenuation time constant τn, and Y0: lag signal value remaining at the radiation non-emission time serving as the base point for the recursive computation before said predetermined operation; and to obtain the corrected radiation detection signals by removing the lag-behind parts based on said impulse response derived from said equations A-C with conditions of the initial values determined from said equation D.

3. A radiographic apparatus as defined in claim 1, characterized in that said apparatus further comprises an irradiation field control device for controlling a size of an irradiation field of the radiation emitted from said radiation emitting device, and said predetermined operation is an irradiation field expansion by said irradiation field control device, said (B) being arranged to execute said stop and acquire the radiation detection signals in time of said non-emission in response to an instruction for the irradiation field expansion, and said (C) being arranged to execute said restart with start of the irradiation field expansion, whereby, after the irradiation field expansion, the time lag removing device removes the lag-behind parts by the recursive computation based on the initial values derived from the radiation detection signals in time of said non-emission, to obtain the corrected radiation detection signals.

4. A radiographic apparatus as defined in claim 3, characterized in that said irradiation field control device is arranged control the size of the irradiation field to be larger before said irradiation field expansion than an image subjected to said recursive computation, and smaller after the irradiation field expansion than the image subjected to the recursive computation.

5. A radiographic apparatus as defined in claim 3, characterized in that, where a residual rate of component n of certain attenuation time constant τn, is expressed as γn, and ratios of time constant component amounts are expressed as γ1 : γ2 : . . . : γn: . . . :γN−1: γN, said time lag removing device is arranged to set the ratios to be constant before and after said irradiation field expansion.

6. A radiographic apparatus as defined in claim 5, characterized in that, for pixels common before and after said irradiation field expansion, pixel values based on the radiation detection signals in time of non-emission are divided for each attenuation time constant, using the ratio of time constant component amounts at an irradiation time before said irradiation field expansion and immediately before the time of non-emission, and each divided value is set as the initial value; and for pixels in a portion newly added by the irradiation field expansion, pixel values based on the radiation detection signals in time of non-emission are divided for each attenuation time constant, using the same ratio of time constant component amounts as used for said common pixels, and each divided value is set as the initial value; whereby, after the irradiation field expansion, the time lag removing device removes the lag-behind parts by the recursive computation based on the respective initial values, to obtain the corrected radiation detection signals.

7. A radiographic apparatus as defined in claim 6, characterized in that said time lag removing device is arranged to carry out the recursive computation, after said irradiation field expansion, for removing the lag-behind parts from the radiation detection signals, based on the following equations A-C:

$$Xk = Yk - \Sigma n = 1 N[Snk] \qquad A$$

$$Tn = -\Delta t / \tau n \qquad B$$

$$Snk = \exp(Tn) \cdot \{\alpha n \cdot [1 - \exp(Tn)] \cdot \exp(Tn) \cdot Sn(k-1)\} \qquad C$$

where Δt: the sampling time interval;
k: a subscript representing a k-th point of time in a sampling time series;
Yk: a radiation detection signal taken at the k-th sampling time;
Xk: a corrected radiation detection signal with a lag-behind part removed from the signal Yk;
Xk−1: a signal Xk taken at a preceding point of time;
Sn(k−1): an Snk at a preceding point of time;
exp: an exponential function;
N: the number of exponential functions with different time constants forming the impulse response;

n: a subscript representing one of the exponential functions forming the impulse response;
αn: an intensity of exponential function n; and
τn: an attenuation time constant of exponential function n;
to determine said initial values as in the following equations D and H, with a sampling point in time of emission before said irradiation field expansion and immediately before the time of non-emission expressed as k':

$$X0=0, Sn0=\gamma n \cdot Y0 \qquad D$$

$$\gamma n = Snk' / \Sigma n = 1 N[Snk'] \qquad H$$

where γn: residual rate of component n of certain attenuation time constant τn;
Y0 : lag signal value remaining at the radiation non-emission time serving as the base point for the recursive computation after said irradiation field expansion (radiation detection signal at the non-emission time); and
Snk': Snk at sampling point k'; and
to obtain the corrected radiation detection signals by removing the lag-behind parts based on said impulse response derived from said equations A-C with conditions of the initial values determined from said equations D and H.

8. A radiation detection signal processing method for taking, at predetermined sampling time intervals, radiation detection signals detected after irradiation of an object under examination, and carrying out signal processing to obtain radiographic images based on the radiation detection signals outputted at the sampling time intervals, characterized in that the radiation detection signal processing method carries out a process of removing lag-behind parts from the radiation detection signals by a recursive computation, on an assumption that a lag-behind part included in each of said radiation detection signals taken at the predetermined sampling time intervals is due to an impulse response formed of a single or a plurality of exponential functions with different attenuation time constants, according to the following steps: (A) in a state where an emission of radiation is started, the lag-behind parts are removed by said recursive computation to obtain corrected radiation detection signals, (B) in response to an instruction for a predetermined operation relating to radiographic imaging, the emission is stopped temporarily, and the recursive computation is stopped temporarily, to acquire radiation detection signals in time of non-emission due to the temporary stop, and (C) with start of said predetermined operation, emission is again, and the recursive computation is started again based on initial values derived from the radiation detection signals in time of said non-emission.

9. A radiation detection signal processing method as defined in claim 8, characterized in that the recursive computation is carried out, before said predetermined operation, for removing the lag-behind parts from the radiation detection signals, based on the following equations A-C:

$$Xk = Yk - \Sigma n = 1 N[Snk] \qquad A$$

$$Tn = -\Delta t / \tau n \qquad B$$

$$Snk = \exp(Tn) \cdot \{\alpha n \cdot [1 - \exp(Tn)] \cdot \exp(Tn) \cdot Sn(k-1)\} \qquad C$$

where Δt: the sampling time interval;
k: a subscript representing a k-th point of time in a sampling time series;
Yk: a radiation detection signal taken at the k-th sampling time;
Xk: a corrected radiation detection signal with a lag-behind part removed from the signal Yk;
Xk−1: a signal Xk taken at a preceding point of time;
Sn(k−1): an Snk at a preceding point of time;

exp: an exponential function;

N: the number of exponential functions with different time constants forming the impulse response;

n: a subscript representing one of the exponential functions forming the impulse response;

αn: an intensity of exponential function n; and

τn: an attenuation time constant of exponential function n;

to determine the initial values for the recursive computation as in the following equation D:

$$X0=0, Sn0=\gamma n \cdot Y0 \qquad \qquad D$$

where γn: residual rate of component n of certain attenuation time constant τn, and Y0 : lag signal value remaining at the radiation non-emission time serving as the base point for the recursive computation before said predetermined operation; and to obtain the corrected radiation detection signals by removing the lag-behind parts based on said impulse response derived from said equations A-C with conditions of the initial values determined from said equation D.

10. A radiation detection signal processing method as defined in claim 8, characterized in that said predetermined operation is an irradiation field expansion, said (B) being arranged to execute said stop and acquire the radiation detection signals in time of said non-emission in response to an instruction for the irradiation field expansion, and said (C) being arranged to execute said restart with start of the irradiation field expansion, whereby, after the irradiation field expansion, the lag-behind parts are removed by the recursive computation based on the initial values derived from the radiation detection signals in time of said non-emission, to obtain the corrected radiation detection signals.

11. A radiation detection signal processing method as defined in claim 10, characterized in that the size of the irradiation field is controlled to be larger before said irradiation field expansion than an image subjected to said recursive computation, and smaller after the irradiation field expansion than the image subjected to the recursive computation.

12. A radiation detection signal processing method as defined in claim 10, characterized in that, where a residual rate of component n of certain attenuation time constant τn is expressed as γn, and ratios of time constant component amounts are expressed as γ1 : γ2 : . . . γn: . . . : γN−1: γN, the ratios are set to be constant before and after said irradiation field expansion.

13. A radiation detection signal processing method as defined in claim 12, characterized in that, for pixels common before and after said irradiation field expansion, pixel values based on the radiation detection signals in time of non-emission are divided for each attenuation time constant, using the ratio of time constant component amounts at an irradiation time before said irradiation field expansion and immediately before the time of non-emission, and each divided value is set as the initial value; and for pixels in a portion newly added by the irradiation field expansion, pixel values based on the radiation detection signals in time of non-emission are divided for each attenuation time constant, using the same ratio of time constant component amounts as used for said common pixels, and each divided value is set as the initial value; whereby, after the irradiation field expansion, the lag-behind parts are removed by the recursive computation based on the respective initial values, to obtain the corrected radiation detection signals.

14. A radiation detection signal processing method as defined in claim 13, characterized in that the recursive computation is carried out, after said irradiation field expansion, for removing the lag-behind parts from the radiation detection signals, based on the following equations A-C:

$$Xk = Yk - \Sigma n=1N[Snk] \qquad \qquad A$$

$$Tn = -\Delta t/\tau n \qquad \qquad B$$

$$Snk = \exp(Tn) \cdot \{\alpha n \cdot [1-\exp(Tn)] \cdot \exp(Tn) \cdot Sn(k-1)\} \qquad C$$

where Δt: the sampling time interval;

k: a subscript representing a k-th point of time in a sampling time series;

Yk: a radiation detection signal taken at the k-th sampling time;

Xk: a corrected radiation detection signal with a lag-behind part removed from the signal Yk;

Xk−1: a signal Xk taken at a preceding point of time;

Sn(k−1): an Snk at a preceding point of time;

exp: an exponential function;

N: the number of exponential functions with different time constants forming the impulse response;

n: a subscript representing one of the exponential functions forming the impulse response;

αn: an intensity of exponential function n; and

τn: an attenuation time constant of exponential function n;

to determine said initial values as in the following equations D and H, with a sampling point in time of emission before said irradiation field expansion and immediately before the time of non-emission expressed as k':

$$X0=0, Sn0=\gamma n \cdot Y0 \qquad \qquad D$$

$$\gamma n = Snk'/\Sigma n=1N[Snk'] \qquad \qquad H$$

where γn: residual rate of component n of certain attenuation time constant τn;

Y0 : lag signal value remaining at the radiation non-emission time serving as the base point for the recursive computation after said irradiation field expansion (radiation detection signal at the non-emission time); and Snk': Snk at sampling point k'; and to obtain the corrected radiation detection signals by removing the lag-behind parts based on said impulse response derived from said equations A-C with conditions of the initial values determined from said equations D and H.

\* \* \* \* \*